(12) United States Patent
Huebner

(10) Patent No.: US 7,578,825 B2
(45) Date of Patent: Aug. 25, 2009

(54) PLACEMENT OF FASTENERS INTO BONE

(75) Inventor: Randall J. Huebner, Beaverton, OR (US)

(73) Assignee: Acumed LLC, Hillsboro, OR (US)

( * ) Notice: Subject to any disclaimer, the term of this patent is extended or adjusted under 35 U.S.C. 154(b) by 174 days.

(21) Appl. No.: 11/109,984

(22) Filed: Apr. 19, 2005

(65) Prior Publication Data

US 2005/0234472 A1 Oct. 20, 2005

Related U.S. Application Data

(60) Provisional application No. 60/563,860, filed on Apr. 19, 2004.

(51) Int. Cl.
*A61B 17/58* (2006.01)
*A61B 17/60* (2006.01)
*A61F 2/00* (2006.01)

(52) U.S. Cl. .................................. 606/104; 606/281

(58) Field of Classification Search .................. 606/61, 606/69–71, 280–299
See application file for complete search history.

(56) References Cited

U.S. PATENT DOCUMENTS

| | | | |
|---|---|---|---|
| 820,503 A | 5/1906 | Krengel et al. | |
| 869,697 A | 10/1907 | Eilhauer et al. | |
| 1,105,105 A | 7/1914 | Sherman | |
| 1,789,060 A | 1/1931 | Weisenbach | |
| 1,889,239 A | 11/1932 | Crowley | |
| 2,243,717 A | 5/1941 | Moreira | |
| 2,406,832 A | 9/1946 | Hardinge | |
| 2,443,363 A | 6/1948 | Townsend et al. | |
| 2,489,870 A * | 11/1949 | Dzus ........................ | 606/73 |
| 2,494,229 A | 1/1950 | Collison | |
| 2,500,370 A | 3/1950 | McKibbin | |
| 2,526,959 A | 10/1950 | Lorenzo | |
| 2,580,821 A | 1/1952 | Nicola | |
| 2,583,896 A | 1/1952 | Siebrandt | |
| 2,737,835 A | 3/1956 | Herz | |
| 3,025,853 A | 3/1962 | Mason | |
| 3,072,423 A | 1/1963 | Charlton | |
| 3,171,518 A | 3/1965 | Bergmann | |
| 3,488,779 A | 1/1970 | Christensen | |
| 3,489,143 A | 1/1970 | Halloran | |
| 3,593,709 A | 7/1971 | Halloran | |
| 3,604,414 A | 9/1971 | Borges | |
| 3,664,022 A | 5/1972 | Small | |
| 3,709,218 A * | 1/1973 | Halloran ..................... | 606/64 |

(Continued)

FOREIGN PATENT DOCUMENTS

AU 89750/91 2/1992

(Continued)

OTHER PUBLICATIONS

McBride S.M.O. Stainless Steel Bone Plates brochure, DePuy, Inc., 1943.

(Continued)

*Primary Examiner*—Thomas C Barrett
*Assistant Examiner*—Andrew Yang
(74) *Attorney, Agent, or Firm*—Kolisch Hartwell, PC

(57) ABSTRACT

System, including methods, apparatus, and kits, for retrograde placement of fasteners into bone.

20 Claims, 4 Drawing Sheets

U.S. PATENT DOCUMENTS

| | | | |
|---|---|---|---|
| 3,716,050 A | 2/1973 | Johnston | |
| 3,741,205 A | 6/1973 | Markolf et al. | |
| 3,842,825 A | 10/1974 | Wagner | |
| 3,866,458 A | 2/1975 | Wagner | |
| 3,900,025 A | 8/1975 | Barnes, Jr. | |
| 3,901,064 A | 8/1975 | Jacobson | |
| 3,939,497 A | 2/1976 | Heimke et al. | |
| 3,965,720 A | 6/1976 | Goodwin et al. | |
| 4,059,102 A * | 11/1977 | Devas ........................ 606/309 |
| 4,187,840 A | 2/1980 | Watanabe | |
| 4,187,841 A | 2/1980 | Knutson | |
| 4,201,215 A | 5/1980 | Crossett et al. | |
| 4,364,382 A | 12/1982 | Mennen | |
| 4,388,921 A | 6/1983 | Sutter et al. | |
| 4,408,601 A | 10/1983 | Wenk | |
| RE31,628 E | 7/1984 | Allgower et al. | |
| 4,457,307 A | 7/1984 | Stillwell | |
| 4,465,065 A | 8/1984 | Gotfried | |
| 4,484,570 A | 11/1984 | Sutter et al. | |
| 4,493,317 A | 1/1985 | Klaue | |
| 4,498,468 A | 2/1985 | Hansson | |
| 4,506,681 A | 3/1985 | Mundell | |
| 4,513,744 A | 4/1985 | Klaue | |
| 4,565,191 A | 1/1986 | Slocu | |
| 4,565,192 A | 1/1986 | Shapiro | |
| 4,565,193 A | 1/1986 | Streli | |
| 4,573,458 A | 3/1986 | Lower | |
| 4,651,724 A | 3/1987 | Berentey et al. | |
| 4,683,878 A | 8/1987 | Carter | |
| 4,703,751 A | 11/1987 | Pohl | |
| 4,718,413 A | 1/1988 | Johnson | |
| 4,730,608 A | 3/1988 | Schlein | |
| 4,736,737 A | 4/1988 | Fargie et al. | |
| 4,743,261 A | 5/1988 | Epinette | |
| 4,750,481 A | 6/1988 | Reese | |
| 4,757,810 A | 7/1988 | Reese | |
| 4,759,350 A | 7/1988 | Dunn et al. | |
| 4,760,843 A | 8/1988 | Fischer et al. | |
| 4,794,918 A | 1/1989 | Wolter | |
| 4,800,874 A | 1/1989 | David et al. | |
| 4,823,780 A | 4/1989 | Odensten et al. | |
| 4,865,025 A | 9/1989 | Buzzi et al. | |
| 4,867,144 A | 9/1989 | Karas et al. | |
| 4,892,093 A | 1/1990 | Zarnowski et al. | |
| 4,893,619 A | 1/1990 | Dale et al. | |
| 4,895,141 A | 1/1990 | Koeneman et al. | |
| 4,903,691 A | 2/1990 | Heinl | |
| 4,917,604 A | 4/1990 | Small | |
| 4,923,471 A | 5/1990 | Morgan | |
| 4,926,847 A | 5/1990 | Luckman | |
| 4,943,292 A | 7/1990 | Foux | |
| 4,955,886 A | 9/1990 | Pawluk | |
| 4,957,497 A | 9/1990 | Hoogland et al. | |
| 4,963,153 A | 10/1990 | Noesberger et al. | |
| 4,964,403 A | 10/1990 | Karas et al. | |
| 4,966,599 A | 10/1990 | Pollock | |
| 4,973,332 A | 11/1990 | Kummer | |
| 4,988,350 A | 1/1991 | Herzberg | |
| 5,002,544 A | 3/1991 | Klaue et al. | |
| 5,006,120 A | 4/1991 | Carter | |
| 5,013,315 A | 5/1991 | Barrows | |
| 5,015,248 A | 5/1991 | Burstein et al. | |
| 5,041,113 A | 8/1991 | Biedermann et al. | |
| 5,042,983 A | 8/1991 | Rayhack | |
| 5,049,149 A | 9/1991 | Schmidt | |
| 5,053,036 A | 10/1991 | Perren et al. | |
| 5,085,660 A | 2/1992 | Lin | |
| 5,113,685 A | 5/1992 | Asher et al. | |
| 5,129,899 A | 7/1992 | Small et al. | |
| 5,133,718 A | 7/1992 | Mao | |
| 5,139,497 A | 8/1992 | Tilghman et al. | |
| 5,147,361 A | 9/1992 | Ojima et al. | |
| 5,151,103 A | 9/1992 | Tepic et al. | |
| 5,154,717 A | 10/1992 | Matsen, III et al. | |
| 5,161,404 A | 11/1992 | Hayes | |
| 5,176,685 A | 1/1993 | Rayhack | |
| 5,190,544 A | 3/1993 | Chapman et al. | |
| 5,190,545 A | 3/1993 | Corsi et al. | |
| 5,197,966 A | 3/1993 | Sommerkamp | |
| 5,201,737 A | 4/1993 | Leibinger et al. | |
| 5,234,431 A | 8/1993 | Keller | |
| 5,236,432 A | 8/1993 | Matsen, III et al. | |
| 5,269,784 A | 12/1993 | Mast | |
| 5,290,288 A | 3/1994 | Vignaud et al. | |
| 5,304,180 A | 4/1994 | Slocum | |
| 5,314,490 A | 5/1994 | Wagner et al. | |
| 5,364,398 A | 11/1994 | Chapman et al. | |
| 5,364,399 A | 11/1994 | Lowery et al. | |
| 5,380,327 A | 1/1995 | Eggers et al. | |
| 5,413,577 A | 5/1995 | Pollock | |
| 5,423,826 A | 6/1995 | Coates et al. | |
| 5,429,641 A | 7/1995 | Gotfried | |
| 5,443,516 A | 8/1995 | Albrektsson et al. | |
| 5,458,654 A | 10/1995 | Tepic | |
| 5,468,242 A | 11/1995 | Reisberg | |
| 5,474,553 A | 12/1995 | Baumgart | |
| 5,487,741 A | 1/1996 | Maruyama et al. | |
| 5,487,743 A | 1/1996 | Laurain et al. | |
| 5,522,902 A | 6/1996 | Yuan et al. | |
| 5,527,311 A | 6/1996 | Proctor et al. | |
| 5,531,745 A | 7/1996 | Ray | |
| 5,534,027 A | 7/1996 | Hodorek | |
| 5,545,228 A | 8/1996 | Kambin | |
| 5,564,302 A | 10/1996 | Watrous | |
| 5,578,036 A | 11/1996 | Stone et al. | |
| 5,586,985 A | 12/1996 | Putnam et al. | |
| 5,591,166 A | 1/1997 | Bernhardt et al. | |
| 5,601,553 A | 2/1997 | Trebing et al. | |
| 5,601,565 A | 2/1997 | Huebner | |
| 5,607,426 A | 3/1997 | Ralph et al. | |
| 5,613,971 A | 3/1997 | Lower et al. | |
| 5,643,261 A | 7/1997 | Schafer et al. | |
| 5,643,265 A | 7/1997 | Errico et al. | |
| 5,647,872 A | 7/1997 | Gilbert et al. | |
| 5,658,283 A | 8/1997 | Huebner | |
| 5,662,655 A | 9/1997 | Laboureau et al. | |
| 5,665,088 A | 9/1997 | Gil et al. | |
| 5,665,089 A | 9/1997 | Dall et al. | |
| 5,674,222 A | 10/1997 | Berger et al. | |
| 5,676,667 A * | 10/1997 | Hausman ................... 606/281 |
| 5,681,313 A | 10/1997 | Diez | |
| 5,702,396 A | 12/1997 | Hoenig et al. | |
| 5,707,372 A | 1/1998 | Errico et al. | |
| 5,707,373 A | 1/1998 | Sevrain et al. | |
| 5,709,682 A | 1/1998 | Medoff | |
| 5,709,686 A | 1/1998 | Talos et al. | |
| 5,718,704 A | 2/1998 | Medoff | |
| 5,718,705 A | 2/1998 | Sammarco | |
| 5,720,502 A | 2/1998 | Cain | |
| 5,722,976 A | 3/1998 | Brown | |
| 5,730,743 A | 3/1998 | Kirsch et al. | |
| 5,733,287 A | 3/1998 | Tepic et al. | |
| 5,735,853 A | 4/1998 | Olerud | |
| 5,741,258 A | 4/1998 | Klaue et al. | |
| 5,741,259 A | 4/1998 | Chan | |
| 5,749,872 A | 5/1998 | Kyle et al. | |
| 5,749,873 A | 5/1998 | Fairley | |
| 5,752,958 A | 5/1998 | Wellisz | |
| 5,766,174 A | 6/1998 | Perry | |
| 5,772,662 A | 6/1998 | Chapman et al. | |
| 5,807,396 A | 9/1998 | Raveh | |
| 5,810,823 A | 9/1998 | Klaue et al. | |
| 5,810,824 A | 9/1998 | Chan | |
| 5,853,413 A | 12/1998 | Carter et al. | |

| Patent | Date | Name | | Patent | Date | Name |
|---|---|---|---|---|---|---|
| D404,128 S | 1/1999 | Huebner | | 6,440,135 B2 | 8/2002 | Orbay et al. |
| 5,855,580 A | 1/1999 | Kreidler et al. | | 6,454,769 B1 | 9/2002 | Wagner et al. |
| 5,871,548 A | 2/1999 | Sanders et al. | | 6,454,770 B1 | 9/2002 | Klaue |
| 5,879,389 A | 3/1999 | Koshino | | 6,458,133 B1 | 10/2002 | Lin |
| 5,902,304 A | 5/1999 | Walker et al. | | 6,503,250 B2 | 1/2003 | Paul |
| 5,904,683 A | 5/1999 | Pohndorf et al. | | 6,508,819 B1 | 1/2003 | Orbay |
| 5,916,216 A | 6/1999 | DeSatnick et al. | | 6,514,274 B1 | 2/2003 | Boucher et al. |
| 5,919,195 A | 7/1999 | Wilson et al. | | 6,520,965 B2 | 2/2003 | Chervitz et al. |
| 5,928,234 A | 7/1999 | Manspeizer | | 6,527,775 B1 | 3/2003 | Warburton |
| 5,931,839 A | 8/1999 | Medoff | | 6,533,789 B1 | 3/2003 | Hall, IV et al. |
| 5,938,664 A | 8/1999 | Winquist et al. | | 6,540,753 B2 | 4/2003 | Cohen |
| 5,941,878 A | 8/1999 | Medoff | | 6,547,790 B2 | 4/2003 | Harkey et al. |
| 5,951,557 A | 9/1999 | Luter | | 6,565,570 B2 | 5/2003 | Sterett et al. |
| 5,954,722 A | 9/1999 | Bono | | 6,592,578 B2 | 7/2003 | Henniges et al. |
| 5,964,763 A | 10/1999 | Incavo et al. | | 6,595,993 B2 | 7/2003 | Donno et al. |
| 5,968,047 A * | 10/1999 | Reed ............ 606/76 | | 6,602,255 B1 | 8/2003 | Campbell et al. |
| 5,973,223 A | 10/1999 | Tellman et al. | | 6,623,486 B1 * | 9/2003 | Weaver et al. ............ 606/69 |
| 6,001,099 A | 12/1999 | Huebner | | 6,623,487 B1 | 9/2003 | Goshert |
| 6,004,323 A | 12/1999 | Park et al. | | 6,682,531 B2 | 1/2004 | Winquist et al. |
| 6,022,350 A | 2/2000 | Ganem | | 6,682,533 B1 | 1/2004 | Dinsdale et al. |
| 6,053,915 A | 4/2000 | Bruchmann | | 6,692,503 B2 | 2/2004 | Foley et al. |
| 6,077,266 A | 6/2000 | Medoff | | 6,695,846 B2 | 2/2004 | Richelsoph et al. |
| 6,077,271 A | 6/2000 | Huebner et al. | | 6,706,046 B2 | 3/2004 | Orbay et al. |
| 6,096,040 A | 8/2000 | Esser | | 6,712,820 B2 | 3/2004 | Orbay |
| 6,096,043 A | 8/2000 | Techiera et al. | | 6,719,759 B2 | 4/2004 | Wagner et al. |
| 6,113,603 A | 9/2000 | Medoff | | 6,730,090 B2 | 5/2004 | Orbay et al. |
| 6,117,160 A | 9/2000 | Bonutti | | 6,736,819 B2 | 5/2004 | Tipirneni |
| 6,123,709 A | 9/2000 | Jones | | 6,767,351 B2 | 7/2004 | Orbay et al. |
| 6,129,728 A | 10/2000 | Schumacher et al. | | 6,793,658 B2 | 9/2004 | LeHuec et al. |
| 6,129,730 A | 10/2000 | Bono et al. | | 6,858,031 B2 | 2/2005 | Morrison et al. |
| 6,139,548 A | 10/2000 | Errico | | 6,866,665 B2 | 3/2005 | Orbay |
| 6,152,927 A | 11/2000 | Farris et al. | | 6,893,444 B2 | 5/2005 | Orbay |
| 6,179,839 B1 | 1/2001 | Weiss et al. | | 7,153,309 B2 * | 12/2006 | Huebner et al. ............ 606/96 |
| 6,183,475 B1 | 2/2001 | Lester et al. | | 2001/0011172 A1 * | 8/2001 | Orbay et al. ............ 606/69 |
| 6,193,721 B1 | 2/2001 | Michelson | | 2002/0032446 A1 | 3/2002 | Orbay |
| 6,197,028 B1 | 3/2001 | Ray et al. | | 2002/0055741 A1 | 5/2002 | Schlapfer et al. |
| 6,206,886 B1 | 3/2001 | Bennett | | 2002/0133172 A1 | 9/2002 | Lambrecht et al. |
| 6,221,073 B1 | 4/2001 | Weiss et al. | | 2002/0143336 A1 | 10/2002 | Hearn |
| 6,224,602 B1 | 5/2001 | Hayes | | 2002/0143338 A1 | 10/2002 | Orbay et al. |
| 6,228,087 B1 | 5/2001 | Fenaroli et al. | | 2002/0147453 A1 | 10/2002 | Gambale |
| 6,235,033 B1 | 5/2001 | Brace et al. | | 2002/0151899 A1 | 10/2002 | Bailey et al. |
| 6,235,034 B1 | 5/2001 | Bray | | 2002/0156474 A1 | 10/2002 | Wack et al. |
| 6,238,396 B1 | 5/2001 | Lombardo | | 2003/0040748 A1 | 2/2003 | Aikins et al. |
| 6,258,092 B1 | 7/2001 | Dall | | 2003/0055429 A1 | 3/2003 | Ip et al. |
| 6,261,291 B1 | 7/2001 | Talaber et al. | | 2003/0083661 A1 | 5/2003 | Orbay et al. |
| 6,273,889 B1 | 8/2001 | Richelsoph | | 2003/0105461 A1 | 6/2003 | Putnam |
| 6,283,969 B1 | 9/2001 | Grusin et al. | | 2003/0149434 A1 | 8/2003 | Paul |
| 6,290,703 B1 | 9/2001 | Ganem | | 2003/0153918 A1 | 8/2003 | Putnam et al. |
| 6,302,883 B1 | 10/2001 | Bono | | 2003/0233093 A1 | 12/2003 | Moles et al. |
| 6,302,884 B1 | 10/2001 | Wellisz et al. | | 2004/0006349 A1 | 1/2004 | Goble et al. |
| 6,302,887 B1 * | 10/2001 | Spranza et al. ............ 606/73 | | 2004/0102775 A1 | 5/2004 | Huebner |
| 6,306,136 B1 | 10/2001 | Baccelli | | 2004/0102776 A1 | 5/2004 | Huebner |
| 6,312,431 B1 | 11/2001 | Asfora | | 2004/0102777 A1 | 5/2004 | Huebner |
| 6,315,779 B1 | 11/2001 | Morrison et al. | | 2004/0102778 A1 | 5/2004 | Huebner |
| 6,322,562 B1 | 11/2001 | Wolter | | 2004/0102788 A1 | 5/2004 | Huebner et al. |
| 6,325,803 B1 | 12/2001 | Schumacher et al. | | 2004/0116930 A1 | 6/2004 | O'Driscoll et al. |
| 6,331,179 B1 | 12/2001 | Freid et al. | | 2004/0127901 A1 | 7/2004 | Huebner et al. |
| 6,336,927 B2 | 1/2002 | Rogozinski | | 2004/0127903 A1 | 7/2004 | Schlapfer et al. |
| 6,338,734 B1 | 1/2002 | Burke et al. | | 2004/0153073 A1 | 8/2004 | Orbay |
| 6,342,055 B1 | 1/2002 | Eisermann et al. | | 2004/0193164 A1 | 9/2004 | Orbay |
| 6,342,075 B1 | 1/2002 | MacArthur | | 2004/0193165 A1 | 9/2004 | Orbay |
| 6,355,036 B1 | 3/2002 | Nakajima | | 2004/0204713 A1 | 10/2004 | Abdou |
| 6,355,042 B2 | 3/2002 | Winquist | | 2004/0220566 A1 | 11/2004 | Bray |
| 6,358,250 B1 * | 3/2002 | Orbay ............ 606/69 | | 2004/0260291 A1 | 12/2004 | Jensen |
| 6,364,881 B1 | 4/2002 | Apgar et al. | | 2004/0260292 A1 | 12/2004 | Orbay et al. |
| 6,364,882 B1 | 4/2002 | Orbay | | 2004/0260293 A1 | 12/2004 | Orbay et al. |
| 6,364,883 B1 | 4/2002 | Santilli | | 2004/0260294 A1 | 12/2004 | Orbay et al. |
| 6,379,354 B1 | 4/2002 | Rogozinski | | 2004/0260295 A1 | 12/2004 | Orbay et al. |
| 6,379,364 B1 | 4/2002 | Brace et al. | | 2005/0049593 A1 | 3/2005 | Duong et al. |
| 6,402,756 B1 | 6/2002 | Ralph et al. | | 2005/0065520 A1 | 3/2005 | Orbay |
| 6,413,259 B1 | 7/2002 | Lyons et al. | | 2005/0065522 A1 | 3/2005 | Orbay |
| 6,428,542 B1 | 8/2002 | Michelson | | 2005/0065523 A1 | 3/2005 | Orbay |
| 6,436,103 B1 | 8/2002 | Suddaby | | 2005/0065524 A1 | 3/2005 | Orbay |

| | | | |
|---|---|---|---|
| 2005/0065528 | A1 | 3/2005 | Orbay |
| 2005/0085818 | A1 | 4/2005 | Huebner |
| 2005/0085819 | A1* | 4/2005 | Ellis et al. ............... 606/71 |
| 2005/0131413 | A1 | 6/2005 | O'Driscoll et al. |
| 2005/0159747 | A1 | 7/2005 | Orbay |
| 2005/0165395 | A1 | 7/2005 | Orbay et al. |
| 2005/0171544 | A1 | 8/2005 | Falkner |
| 2005/0182405 | A1 | 8/2005 | Orbay et al. |
| 2005/0182406 | A1 | 8/2005 | Orbay et al. |
| 2005/0187551 | A1 | 8/2005 | Orbay et al. |
| 2005/0192578 | A1 | 9/2005 | Horst |
| 2005/0234458 | A1 | 10/2005 | Huebner |

FOREIGN PATENT DOCUMENTS

| | | |
|---|---|---|
| CH | 611 147 | 5/1979 |
| DE | 2515430 | 11/1975 |
| DE | 4201531 | 7/1993 |
| DE | 4343117 | 6/1995 |
| EP | 0 053 999 | 6/1982 |
| EP | 0 410 309 | 1/1991 |
| EP | 0471418 A1 | 2/1992 |
| EP | 0362049 B1 | 5/1992 |
| EP | 1 250 892 A2 | 9/2003 |
| EP | 1 250 892 A3 | 9/2003 |
| FR | 742618 | 3/1933 |
| FR | 2254298 | 7/1975 |
| FR | 2367479 | 5/1978 |
| FR | 2405705 | 5/1979 |
| FR | 2405706 | 5/1979 |
| FR | 2406429 | 5/1979 |
| FR | 2472373 | 7/1981 |
| FR | 2674118 | 9/1992 |
| GB | 2245498 | 1/1992 |
| SU | 610518 | 6/1978 |
| SU | 718097 | 2/1980 |
| SU | 862937 | 9/1981 |
| SU | 897233 | 1/1982 |
| SU | 1049054 | 10/1983 |
| SU | 1130332 | 12/1984 |
| SU | 1192806 | 11/1985 |
| SU | 1223901 | 4/1986 |
| SU | 1225556 | 4/1986 |
| SU | 1544406 | 2/1990 |
| SU | 1630804 | 2/1991 |
| SU | 1644932 | 4/1991 |
| SU | 1683724 | 10/1991 |
| SU | 1711859 A | 2/1992 |
| SU | 1734715 A1 | 5/1992 |
| WO | WO82/01645 | 5/1982 |
| WO | WO87/02572 | 5/1987 |
| WO | WO88/03781 | 6/1988 |
| WO | WO96/29948 | 10/1996 |
| WO | WO97/47251 | 12/1997 |
| WO | WO01/21083 A1 | 3/2001 |
| WO | WO01/62136 A3 | 8/2001 |

OTHER PUBLICATIONS

Bone Plates brochure, Vitallium, Mar. 1948.
Dupont Distal Humeral Plates brochure, Howmedica Inc., 1990.
The Arnett-TMP* Titanium Miniplating System brochure, Techmedica, Inc., 1989.
Techmedica Bioengineers Keep Tabs on Your Needs brochure, Techmedica, Inc., 1991.
*Biological Plating: A New Concept to Foster Bone Healing*, Synthes (USA), 1991.
*A Comparison of Unicortical and Bicortical End Screw Attachment of Fracture Fixation Plates*, Beaupre et al., *Journal of Orthopaedic Trauma*, vol. 6, No. 3, pp. 294-300, 1992.
Ace 4.5/5.0 mm Titanium Cannulated Screw and Reconstruction Plate System surgical technique brochure, Ace Medical Company, 1992.
Ace 4.5/5.0 mm Titanium Cannulated Screw and Reconstruction Plate System simplified fracture fixation brochure, Ace Medical Company, 1992.
Ace Titanium 3.5/4.0 mm Screw and Plate System with the Ace 3.5 mm Universal Ribbon CT/MRI compatible fixation brochure, Ace Medical Company, 1992.
Treatment of Three- and Four-Part Fractures of the Proximal Humerus with a Modified Cloverleaf Plate, Esser, *Journal of Orthopaedic Trauma*, vol. 8, No. 1, pp. 15-22, 1994.
Treatment by Plates of Anteriorly Displaced Distal Radial Fractures, Ducloyer, *Fractures of the Distal Radius*, pp. 148-152, 1995.
Management of Comminuted Distal Radial Fractures, Jupiter et al., *Fractures of the Distal Radius*, pp. 167-183, 1995.
Open Reduction of Intra-Articular Fractures of the Distal Radius, Amadio, *Fractures of the Distal Radius*, pp. 193-202, 1995.
May Anatomical bone Plates: Plates, Bone Screws and Instruments brochure, pp. 3-4 and 10-15, Waldemar Link GmbH & Co., 1995.
Forte Distal Radial Plate System brochure, Zimmer, Inc., 1995.
Design and Biomechanics of a Plate for the Distal Radius, Gesensway et al., *Journal of Hand Surgery*, vol. 20, No. 6, pp. 1021-1027, 1995 (abstract only provided).
Ace Symmetry Titanium Upper Extremity Plates surgical technique brochure, Ace Medical Company, 1996.
The Ace Symmetry Titanium Upper Extremity Plates new product release brochure, Ace Medical Company, 1996.
*Fractures of the Distal Radius: A Practical Approach to Management*, Fernandez et al., pp. 103-188, 1996.
Titanium Distal Radius Instrument and Implant Set standard contents description pages, Synthes, Mar. 1997.
Small Titanium Plates overview page, Synthes, p. 2a-33, Mar. 1997.
Prospective Multicenter Trial of a Plate for Dorsal Fixation of Distal Radius Fractures, Ring et al., *The Journal of Hand Surgery*, vol. 22A, No. 5, pp. 777-784, Sep. 1997.
Treatment of Displaced Intra-Articular Fractures of the Distal End of the Radius With Plates, Fitoussi et al., *The Journal of Bone and Joint Surgery*, vol. 79, No. 9, pp. 1303-1312, 1997 (abstract only provided).
The Titanium Distal Radius Plate, technique guide, Synthes (USA), 1997.
TriMed Wrist Fixation System brochure, TriMed, Inc., 1997.
SCS/D Distal Radius Plate System brochure, Avanta Orthopaedics, 1997.
Biomechanical Evaluation of the Schuhli Nut, Kolodziej, et al., *Clinical Orthopaedics and Related Research*, vol. 347, pp. 79-85, Feb. 1998.
Congruent Distal Radius Plate System description, Acumed, Inc., Mar. 4, 1998.
Intra-Articular Fractures of the Distal Aspect of the Radius, Trumble et al., *Journal of Bone and Joint Surgery*, vol. 80A, No. 4, pp. 582-600, Apr. 1998.
Complications of the AO/ASIF Titanium Distal Radius Plate System (π Plate) in Internal Fixation of the Distal Radius: A Brief Report, Kambouroglou et al., *Journal of Hand Surgery*, vol. 23A, No. 4, pp. 737-741, Jul. 1998.
SCS/V Distal Radius Plate Volar brochure, Avanta Orthopaedics, 1998.
*LISS: Less Invasive Stabilization System*, Krettek et al., Dialogue, p. 3, Jan. 1999.
*Less Invasive Stabilization System LISS*, surgical technique, Synthes/Mathys, Feb. 23, 1999.
Salvage of Tibial Pilon Fractures Using Fusion of the Ankle with a 90° Cannulated Blade Plate: A Preliminary Report, Morgan et al., *Foot & Ankle International*, vol. 20, No. 6, pp. 375-378, Jun. 1999.
Delayed Rupture of the Flexor Pollicis Longus Tendon After Inappropriate Placement of the π Plate on the Volar Surface of the Distal Radius, Nunley et al., *Journal of Hand Surgery*, vol. 24, No. 6, pp. 1279-1280, Nov. 1999.
*Scaphoid Protocols Using the Acutrak® Bone Screw System* brochure, Toby, published by Acumed, Inc., Dec. 7, 1999.
TiMAX Pe.R.I. Small Fragment Upper Extremity description pages, DePuy ACE Medical Company, 1999.
The Distal Radius Plate Instrument and Implant Set technique guide, Synthes (USA), 1999.

Outcome Following Nonoperative Treatment of Displaced Distal Radius Fractures in Low-Demand Patients Older Than 60 Years, Young, *Journal of Hand Surgery*, vol. 25A, No. 1, pp. 19-28, Jan. 2000.

Comparison of Three Different Plating Techniques for the Dorsum of the Distal Radius: A Biomechanical Study, Peine et al., *Journal of Hand Surgery*, vol. 25A, No. 1, pp. 29-33, Jan. 2000.

Distal Radial Metaphyseal Forces in an Extrinsic Grip Model: Implications for Postfracture Rehabilitation, Putnam et al., *Journal of Hand Surgery*, vol. 25A, No. 3, pp. 469-475, May 2000.

Single Unit Osteosynthesis brochure, Surfix Technologies, Sep. 2000.

*Congruent Plate System*, surgical technique, Acumed LLC, Dec. 18, 2000.

Supracondylar Cable Plate brochure, Biomet Orthopedics, Inc., 2000.

Principle-Based Internal Fixation of Distal Humerus Fractures, Sanchez-Sotelo et al., *Techniques in Hand & Upper Extremity Surgery*, vol. 5, No. 4, pp. 179-187, Dec. 2001.

TriMed Wrist Fixation System internet description pages, TriMed, Inc., 2001.

Titanium Distal Radius Plates description page, Synthes (USA), 2001.

Locon-T Distal Radius Plating System case study and surgical method, Wright Medical Technology, Inc., 2001.

Congruent Distal Radius Plate System, brochure, Acumed LLC, May 1, 2002.

Congruent Plate System—The Mayo Clinic Congruent Elbow Plates brochure, Acumed, Inc., May 7, 2002.

Internal Fixation in Osteoporotic Bone, An, p. 276, Jul. 2002.

Modular Hand System brochure, Acumed, Inc., Aug. 2002.

Modular Hand System brochure, Acumed, Inc., Sep. 2002.

Internal Fixation in Osteoporotic Bone, An, Y.H., p. 83, 2002.

Periarticular Plating System brochure, Zimmer, Inc., 2002.

Jplate Diaphysis Plates for Japanese brochure, Mizuho Co., Ltd., 2002.

An Axially Mobile Plate for Fracture Fixation, Abel et al., *Internal Fixation in Osteoporotic Bone*, pp. 279-283, 2002.

The Use of Interlocked 'Customised' Blade Plates in the Treatment of Metaphyseal Fractures in Patients with Poor Bone Stock, Palmer et al., *Injury, Int. J. Care Injured*, vol. 31, pp. 187-191, 2002.

3.5 mm LCP™ Proximal Humerus Plate technique guide, Synthes (USA), 2002.

Open Reduction and Internal Fixation of Unstable Distal Radius Fractures: Results Using the Trimed Fixation System, Konrath et al., *Journal of Orthopaedic Trauma*, vol. 16, No. 8, pp. 578-585, 2002.

Locon-T Distal Radius Plating System brochure, Wright Medical Technology, Inc., 2002.

Distal Radius Fracture, Tornetta, *Journal of Orthopaedic Trauma*, vol. 16, No. 8, pp. 608-611, 2002.

Comparison of Different Distal Radius Dorsal and Volar Fracture Fixation Plates: A Biomechanical Study, Osada et al., *Journal of Hand Surgery*, vol. 28A, No. 1, pp. 94-104, Jan. 2003.

Titanium Wire Plate Osteosynthesis System According to Dr. Gahr internet printout, Erothitan Titanimplantate AG, print date Feb. 6, 2003.

*Tendon Function and Morphology Related to Material and Design of Plates For Distal Radius Fracture Fixation: Canine Forelimb Model*, Turner et al., Orthopaedic Research Society, Feb. 2003.

Fractures of the Distal Aspect of the Radius: Changes in Treatment Over the Past Two Decades, Simic, *Journal of Bone and Joint Surgery*, vol. 85-A, No. 3, pp. 552-564, Mar. 2003.

Palmar Plate Fixation of AO Type C2 Fracture of Distal Radius Using a Locking Compression Plate—A Biomechanical Study in a Cadaveric Model, Leung et al., *Journal of Hand Surgery*, vol. 28B, No. 3, pp. 263-266, Jun. 2003.

*Bilder* internet printout, Martin GmbH & Co. KG, print date Sep. 5, 2003.

International Search Report for PCT Patent Application Serial No. PCT/US03/22904, Dec. 4, 2003.

The Use of a Locking Custom Contoured Blade Plate for Peri-Articular Nonunions, Harvey et al., *Injury. Int. J. Care Injured*, vol. 34, pp. 111-116, 2003.

Salvage of Distal Tibia Metaphyseal Nonunions With the 90° Cannulated Blade Plate, Chin et al., *Clinical Orthopaedics and Related Research*, No. 409, pp. 241-249, 2003.

Functional Outcome and Complications Following Two Types of Dorsal Plating for Unstable Fractures of the Distal Part of the Radius, Rozental et al., *Journal of Bone and Joint Surgery*, vol. 85, No. 10, pp. 1956-1960, 2003 (abstract only provided).

*Fixation of Unstable Fractures of the Volar Rim of the Distal Radius with a Volar Buttress Pin®*, Hooker et al., 2003.

Results of Palmar Plating of the Lunate Facet Combined with External Fixation for the Treatment of High-Energy Compression Fractures of the Distal Radius, Ruch et al., *J. Orthop. Trauma*, Vo. 18, No. 1, pp. 28-33, Jan. 2004.

*Rib Securing Clamped Plate*, internet printout, Sanatmetal, print date Sep. 22, 2004.

*Zespol Bone Screws*, in *Mikromed—Catalogue 2004* (Nov. 2004), available at http://www.mikromed.pl/katalog/Main/main_eng.htm and http://www.mikromed.pl/katalog/zespol_eng/wkrety.htm.

*Zespol Bone Plates*, in *Mikromed—Catalogue 2004* (Nov. 2004), available at http://www.mikromed.pl/katalog/Main/main_eng.htm and http://www.mikromed.pl/katalog/zespol_eng/plytki.htm.

SmartLock Locking Screw Technology, advertisement, *The Journal of Hand Surgery*, vol. 30A, No. 1, Jan. 2005.

*Synthes Volar Distal Radius Locking Plate*, internet description page, Orthocopia, LLC, 2004.

*Acromio-Clavicular Plates*, description page, author and date unknown.

*Acroplate*, aap Impantate AG, p. 37, date unknown.

*ECT Internal Fracture Fixation*, brochure, Zimmer, Inc., undated.

*ECT Internal Fracture Fixation System*, order information brochure, Zimmer, Inc., undated.

*NexGen Osteotomy System (OS) surgical technique*, brochure, Zimmer, Inc., undated.

*Esser Complete Distal Radius Plate System*, undated.

*Proximal Humerus Fractures operative technique*, Esser, undated.

*Spider™ and Mini-Spider™ Limited Wrist Fusion System* brochure, Kinetics Medical Incorporated, undated.

*Spider™ Limited Wrist Fusion System* brochure, Kinetics Medical Incorporated, undated.

*The Titanium Volar Distal Radius Plate*, Synthes, date unknown.

*VAL Plate* description page, US Implants, undated.

*Zuelzer Hook Plates* description page, Codman & Shurtleff, Inc., p. 808, undated.

\* cited by examiner

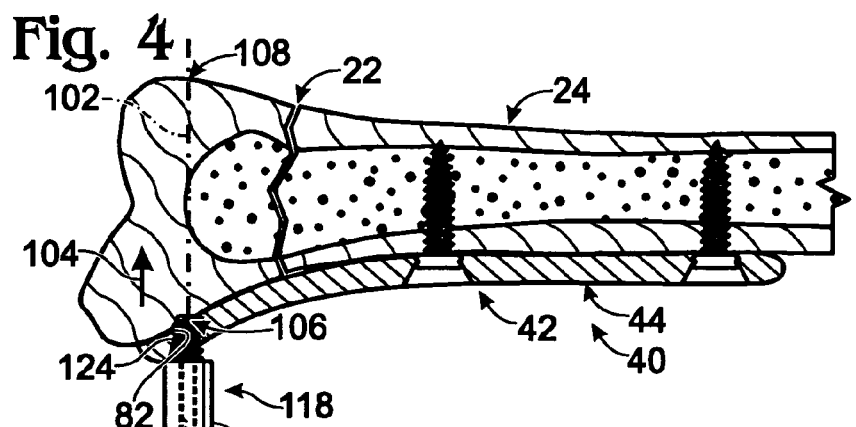
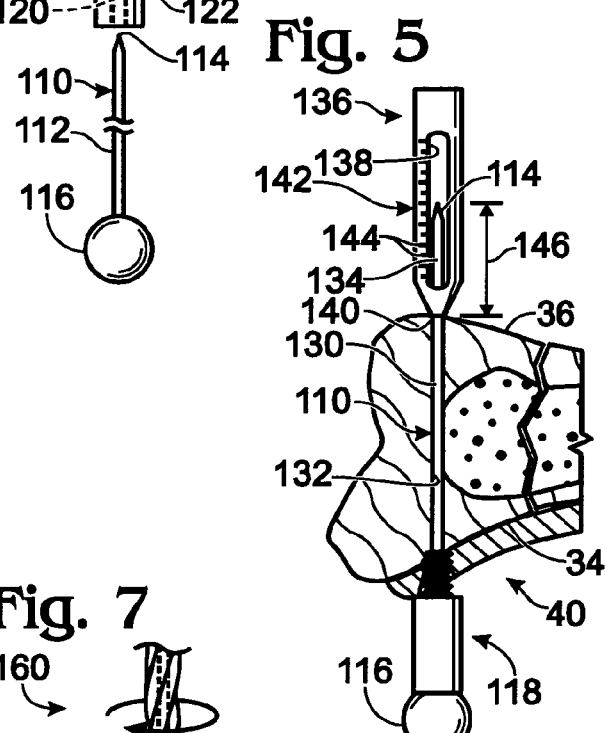
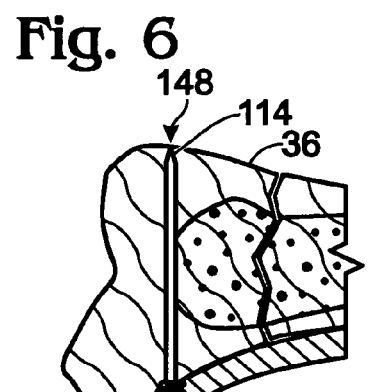
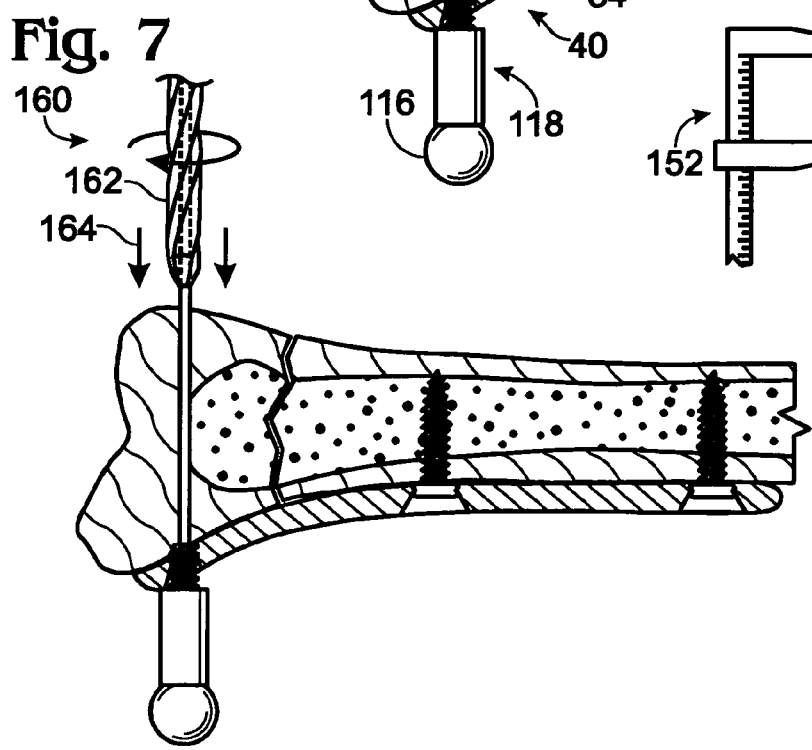

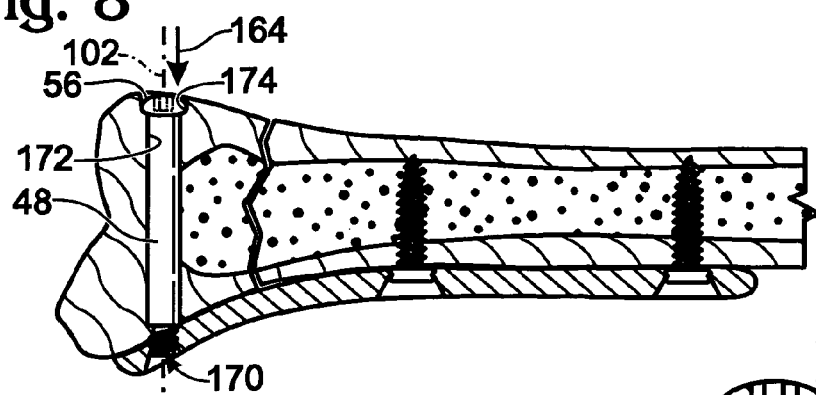
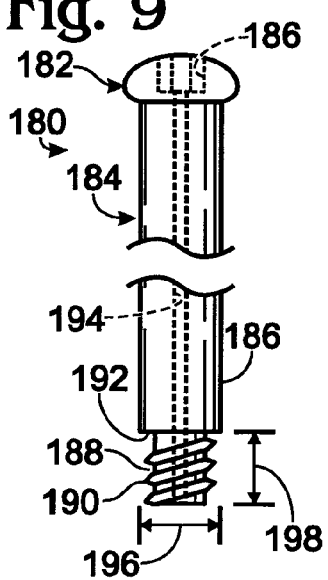
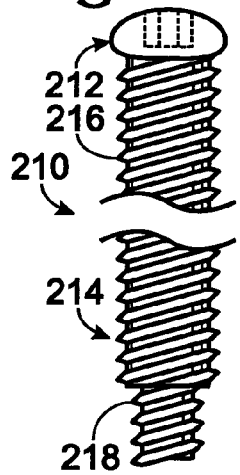
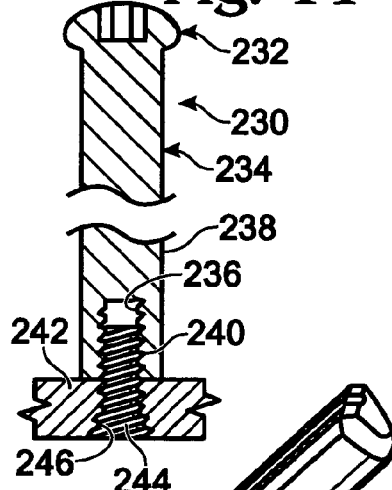
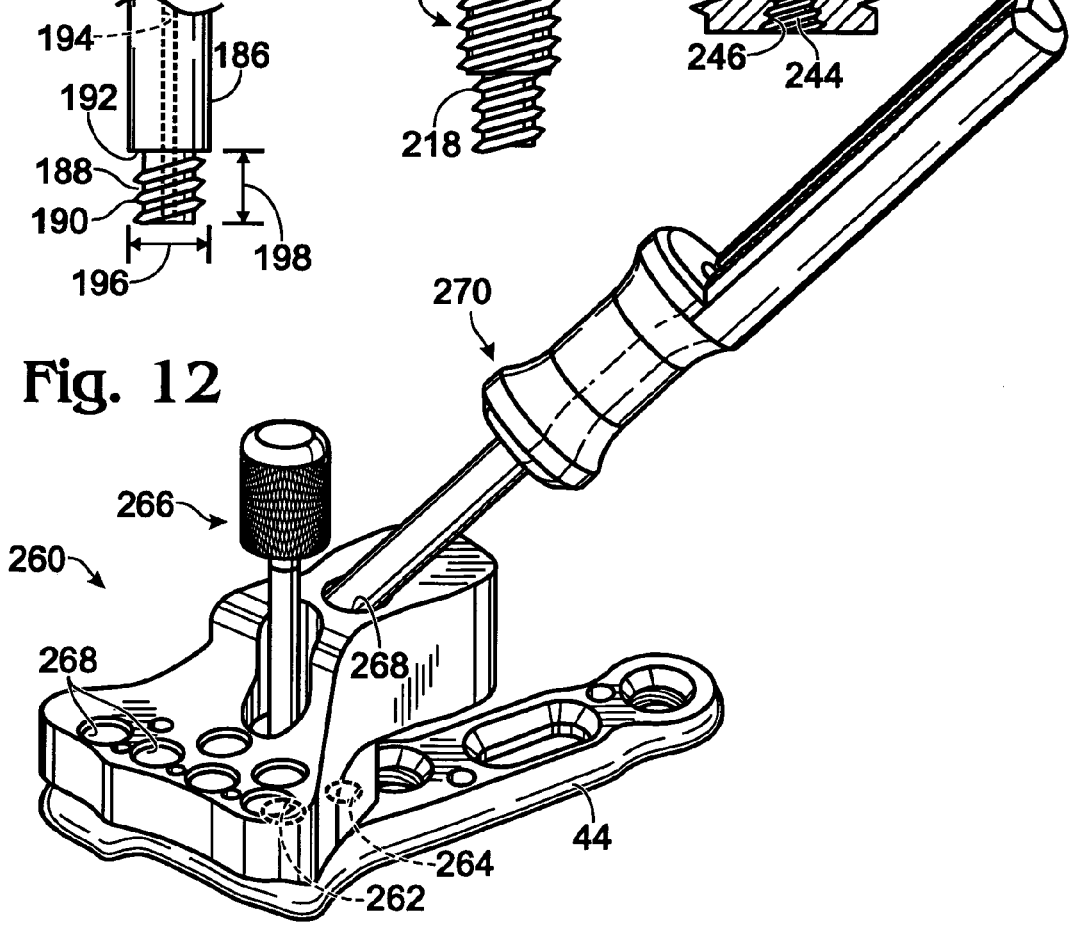

PLACEMENT OF FASTENERS INTO BONE

CROSS-REFERENCE TO PRIORITY APPLICATION

This application is based upon and claims the benefit under 35 U.S.C. § 119(e) of the following U.S. provisional patent application, which is incorporated herein by reference in its entirety for all purposes: Ser. No. 60/563,860, filed Apr. 19, 2004.

CROSS-REFERENCES TO RELATED APPLICATIONS

This application incorporates by reference the following U.S. patent applications: Ser. No. 10/716,719, filed Nov. 19, 2003; Ser. No. 10/717,015, filed Nov. 19, 2003; Ser. No. 10/717,399, filed Nov. 19, 2003; Ser. No. 10/717,401, filed Nov. 19, 2003; Ser. No. 10/717,402, filed Nov. 19, 2003; Ser. No. 10/731,173, filed Dec. 8, 2003; Ser. No. 10/968,850, filed Oct. 18, 2004; and Ser. No. 11/071,050, filed Feb. 28, 2005.

INTRODUCTION

The human skeleton is composed of 206 individual bones that perform a variety of important functions, including support, movement, protection, storage of minerals, and formation of blood cells. To ensure that the skeleton retains its ability to perform these functions, and to reduce pain and disfigurement, bones that become damaged should be repaired promptly and properly. Typically, a fractured or cut bone is treated using a fixation device, which reinforces the bone and keeps it aligned during healing. Fixation devices may include external fixation devices (such as casts and fixators) and/or internal fixation devices (such as bone plates, rods, and/or bone screws), among others.

Bone plates are sturdy internal devices, usually made of metal, that mount directly to the bone adjacent a fracture (or other bone discontinuity). To use a bone plate to repair a discontinuity of a bone, a surgeon typically (1) selects an appropriate plate, (2) reduces the discontinuity (e.g., sets the fracture), and (3) fastens the plate to bone fragments disposed on opposite sides of the discontinuity using suitable fasteners, such as screws and/or wires, so that the bone plate spans the discontinuity and the bone fragments are fixed in position. Each fastener generally is placed through an opening in the bone plate and then into bone.

The radius is one of two long bones found in the human forearm. The radius, like other bones, is susceptible to a variety of fractures and other dislocations. For example, distal fractures of the radius are a common result of forward falls, with the palms facing downward, particularly among the elderly. In such falls, force exerted on the distal radius at impact frequently produces dorsal displacement of one or more bone fragments created distal to the fracture site. Internal fixation of such dorsally displaced bone fragments using bone plates has proved problematic.

Internal fixation may be performed dorsally. In this approach, a surgeon may apply a reducing force on the fracture by attaching a bone plate to the dorsal side of the radius. However, unless the bone plate has a very low profile, dorsal tendons overlying the bone plate may rub against it, producing tendon irritation or even tendon rupture.

Alternatively, internal fixation may be performed volarly. In this approach, a surgeon may attach a bone plate to the volar side of the radius. The volar side of the radius may be more accessible surgically and defines a distal pocket in which the distal portion of the bone plate may be disposed. Accordingly, the bone plate may be less obtrusive and may produce less tendon irritation after placement, even if the bone plate is thicker and sturdier.

Despite the potential advantages of volar fixation, attachment of the bone plate to the volar side of the fractured radius may complicate reduction of the fracture. The distal radius of elderly patients in particular generally contains porous bone of poor quality. Accordingly, bone screws inserted into the distal radius from openings in the bone plate may not achieve adequate purchase in the bone to hold distal bone fragments in position against the bone plate. Moreover, these bone screws may be unable to gain sufficient purchase in bone to pull bone fragments volarly toward the plate to aid in reduction of the fracture.

SUMMARY

The present teachings provide a system, including methods, apparatus, and kits, for retrograde placement of fasteners into bone.

BRIEF DESCRIPTION OF THE DRAWINGS

FIG. 4 is a sectional view of the system of FIG. 2, taken generally along line 4-4 of FIG. 3 in the absence of the retrograde fastener, with the system configured to form of an exemplary guide path extending through the radius, in accordance with aspects of the present teachings.

FIG. 5 is a sectional view of the system of FIG. 2, taken generally as a fragment of FIG. 4, after exemplary guide path formation by insertion of a guide member through the bone and with an exemplary measuring device positioned to measure a portion of the guide member disposed outside the bone, in accordance with aspects of the present teachings.

FIG. 6 is a sectional view of the system of FIG. 2, taken generally as in FIG. 5, with another exemplary measuring device positioned to measure a different portion of the guide member disposed outside the bone, in accordance with aspects of the present teachings.

FIG. 7 is a sectional view of the system of FIG. 2, taken generally as in FIG. 4, with an exemplary drill bit received over the guide member and positioned to form a hole in the bone, in accordance with aspects of the present teachings.

FIG. 8 is a sectional view of the system of FIG. 2, taken generally as in FIG. 4, with an exemplary retrograde fastener received in the bone and engaged with the bone plate through a leading region of the retrograde fastener, in accordance with aspects of the present teachings.

FIG. 9 is a fragmentary view of an exemplary retrograde fastener, in accordance with aspects of the present teachings.

FIG. 10 is a fragmentary view of another exemplary retrograde fastener, in accordance with aspects of the present teachings.

FIG. 11 is a fragmentary view of yet another exemplary retrograde fastener coupled to an implant with an exemplary bridge fastener, in accordance with aspects of the present teachings.

FIG. 12 a view of an exemplary guide device coupled to the bone plate of FIG. 3, in accordance with aspects of the present teachings.

DETAILED DESCRIPTION

The present teachings provide a system, including methods, apparatus, and kits, for retrograde placement of fasteners into bone. The retrograde placement of each fastener may be along a guide path that extends through bone and may be in a direction opposite to that in which the guide path was formed. The guide path may be formed, for example, by placement of a guide member, such as wire, into the bone. In some examples, the guide member may be inserted through bone, from an entry or start site adjacent and/or defined by an implant, such as a bone plate, disposed adjacent the bone, to an exit or end site spaced from the implant. The fastener, such as a bone screw, thus may enter the bone along the guide path, adjacent the exit or end site, from a position outside a footprint defined by the implant on bone. The fastener after entering bone, then may approach the implant from an inner surface of the implant and enter an opening of the implant from adjacent the inner surface, for coupling to the implant, such as through threaded engagement between a leading region of the fastener and an internal thread of the implant. In some examples, retrograde placement may position a head of the fastener in a spaced relation to the implant, such as in engagement with a bone surface region (natural or engineered) that generally opposes the implant on the bone. Overall, retrograde placement of one or more fasteners to couple bone to an implant may provide a number of advantages over placement only in a forward direction, such as (1) more options for fracture reduction, (2) better fixation of poor quality bone, (3) improved bone healing, and/or (4) better compression of bone against the implant, among others.

The following sections describe further aspects of the present teachings, including, among others, (I) overview of an exemplary system for retrograde fastener placement, (II) overview of an exemplary method of retrograde fastener placement, (III) guide paths and formation of guide paths, (IV) fasteners and fastener placement, (V) orthopedic implants, (VI) kits, and (VII) examples.

I. Overview of an Exemplary System for Retrograde Fastener Placement

Figure 1:
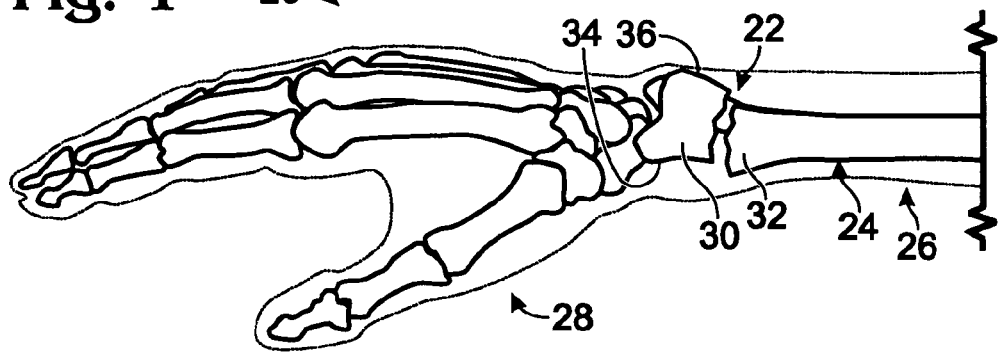
FIG. 1 is a lateral view of the bones of the right hand and distal forearm in which the radius has suffered a Colles' fracture, displacing a distal fragment of the radius dorsally.
Figure 2:
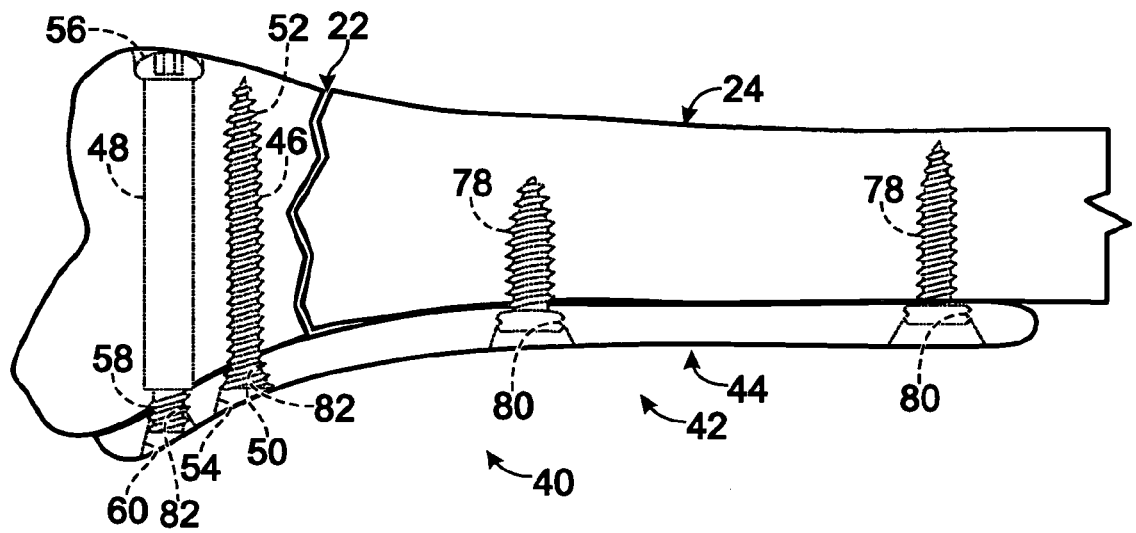
FIG. 2 is a lateral view of an exemplary system for fixing the Colles' fracture of FIG. 1 utilizing a bone plate secured to the radius with forward fasteners and a retrograde fastener, in accordance with aspects of the present teachings.
Figure 3:
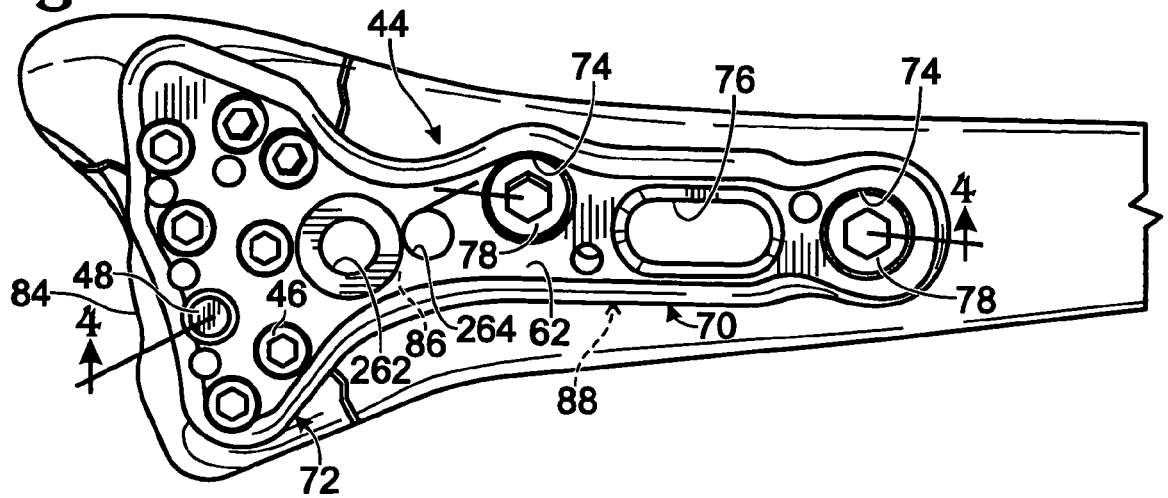
FIG. 3 is a volar view of the system of FIG. 2.

This section describes an exemplary system for retrograde (and/or forward) placement of fasteners into bone, to (and/or from) an implant; see FIGS. 1-3.

FIG. 1 shows an upper right extremity 20 exhibiting a Colles' fracture 22, which is a common fracture of a distal region of a radius bone 24. Colles' fracture is an exemplary fracture that may be treated with an implantable fixation device, such as a bone plate, coupled to a fastener(s) disposed in a retrograde orientation in the radius bone. The position of the fracture is indicated relative to the skin, shown in phantom outline, of the distal forearm 26 and hand 28. In Colles' fracture 22, a smaller, distal bone fragment 30 may be displaced dorsally from a larger, proximal bone fragment 32 of the radius. Colles' fracture 22 may be reduced and then fixed, for example, by installation of a bone plate on the volar (anterior or palm-side) surface 34 and/or on the dorsal (posterior or back-side) surface 36 of the radius.

FIG. 2 shows an exemplary system 40 for fixing a fractured bone, such a radius 24 with Colles' fracture 22, using retrograde fastener placement. The system may include an implant 42, such as a bone plate 44, disposed on an exterior surface of the bone and secured to the bone using one or more "forward" (bone-oriented) fasteners 46, and/or one or more "retrograde" (implant-oriented) fasteners 48. The terms "forward" and "retrograde" are used herein to indicate the head-to-tip direction in which a fastener is oriented (and/or placed) relative to the implant and bone. Forward fasteners may have a head 50 disposed adjacent and/or engaged with the implant and a leading end region 52 spaced from the implant. Forward placement of a fastener may advance the leading end region of the fastener through an opening 54 in the implant and then into the bone. Retrograde fasteners may have a head 56 spaced from the implant, generally across a bone, and a leading end region 58 disposed adjacent and/or engaged with the implant. Retrograde placement of a fastener may advance the leading end region of the fastener through the bone and then into an opening 60 of the implant. In some examples, the same opening(s) of an implant may be configured to be used alternatively for forward placement or retrograde placement of fasteners in opposite directions to achieve opposite fastener orientations.

FIG. 3 shows bone plate 44 from an outer surface 62 of the bone plate. The bone plate may include a body portion 70 joined to a head portion 72. The body portion may be disposed, for example, in a generally longitudinal orientation on the volar surface of the radius. The body portion may include one or more openings, such a circular openings 74 and/or elongate opening 76 that receive fasteners, such as bone screws 78, to secure the body portion to a proximal fragment of the radius bone (also see FIG. 2). The openings of the body portion may include (or lack) an internal thread 80 (see FIG. 2) or other suitable retention structure to lock the bone screws to the body portion. The head portion may be disposed distal to the body portion with the bone plate disposed on the radius, and at least partially distal to one or more fractures (or other discontinuities) in the radius. The head portion also may include a plurality of openings, with any suitable subset (or all) of the openings of the head portion having an internal thread 82 (see FIG. 2). Any of the openings in the body or head portion may receive a forward or retrograde fastener. In the present illustration, retrograde fastener 48 is engaged with the head portion of the bone plate, generally towards a medial side of the radius bone and adjacent a lunate facet 84 of the radius bone (the region of the radius that articulates with the lunate bone).

Bone plate 44 may have an inner surface 86 and may define a footprint 88 on the radius bone. The "footprint," as used herein, is a surface region of the radius bone corresponding in size, shape, and position to the bone plate. The footprint is generally faced by the inner surface of the bone plate, and apposed to and/or in contact with the bone plate's inner surface. Further aspects of bone plate 44 and other bone plates suitable for fixation of the distal radius or other bones, and capable of receiving a retrograde fastener, are described in the following U.S. patent applications, which are incorporated herein by reference: Ser. No. 10/716,719, filed Nov. 19, 2003; Ser. No. 10/717,015, filed Nov. 19, 2003; Ser. No. 10/717,399, filed Nov. 19, 2003; Ser. No. 10/717,401, filed Nov. 19, 2003; Ser. No. 10/717,402, filed Nov. 19, 2003; Ser. No. 10/731,173, filed Dec. 8, 2003; Ser. No. 10/968,850, filed Oct. 18, 2004; and Ser. No. 11/071,050, filed Feb. 28, 2005.

II. Overview of an Exemplary Method of Retrograde Fastener Placement

FIGS. 4-8 show exemplary configurations representing or illustrating steps of a method of retrograde fastener placement. The method steps shown and described here may be performed in any suitable order, in any suitable combination, and any suitable number of times. This method may be used to couple the retrograde fastener to an implant, such as implant 42 (bone plate 44), disposed on a bone (such as radius bone 24), to provide or facilitate bone fixation.

The bone may include a discontinuity spanned by the implant, such as an extra-articular fracture 22 (and/or an intra-articular fracture (a fracture including the articular surface)). In some examples, the discontinuity may be at least partially or completely reduced (e.g., the fracture set) before performing the method of coupling the fastener to the implant, as in the present illustration. In some examples, the coupling of the fastener may provide partial or substantial reduction of the discontinuity, as shown and described in the following provisional patent application, which is incorporated herein by reference: Ser. No. 60/563,860, filed Apr. 19, 2004.

FIG. 4 shows system 40 configured to form an exemplary guide path extending through the bone along a guide axis 102. The guide path may be formed progressively, in a first direction 104, from a start (or entry) site 106 disposed adjacent the implant to an end (or exit) site 108 spaced from the implant. In particular, a guide member 110, such as a wire 112, may be inserted through the bone from the start site to the end site (and generally beyond the end site). The guide member may include a sharp tip 114 and/or cutting edge that facilitates insertion of the wire with a driver. The guide member also may include a stop structure 116 (such as an enlarged proximal end region) that restricts advancement of the guide member through the bone at a predefined position of the guide member.

The guide path may be defined, prior to its formation, by a guide structure 118 coupled to the implant. The guide structure may, for example, be a guide channel, such as a channel 120 defined by a cannula or tube 122 having an axial bore aligned with an opening of the bone plate and generally apposed thereto. In some examples, the channel may have a diameter substantially corresponding to that of the guide member (but generally slightly larger to permit sliding of the guide member along the channel). Accordingly, the guide structure may center the guide member within the guide structure and with respect to an opening of the bone plate, so that the guide member and the opening are arranged concentrically. The guide structure also may include a coupling mechanism, such as an external thread 124, that engages an internal thread 82 of the implant opening. In some examples, the guide structure may be coupled to the implant through a coupling mechanism disposed in a spaced relation to the opening (e.g., see Example 2), so that the guide structure does not occupy the opening and/or engage an internal thread thereof, for placement of a retrograde fastener into the opening with the guide structure coupled to the implant.

FIG. 5 shows system 40 after formation of an exemplary guide path 130. The guide path may be considered to be created by the guide member itself and/or by a bore 132 in the bone formed by insertion of the guide member (or by drilling). To form the guide path, guide member 110 may be placed (inserted) through the bone, between generally opposing surfaces of the bone. In the present illustration, the guide member has been inserted into the bone, from volar surface 34 to dorsal surface 36 of the bone.

The guide member may be advanced any suitable distance out of bone. For example, after formation of the guide path, the guide member may be extended farther, through overlying soft tissue, until the guide member protrudes visibly from the skin. The visible guide member thus may mark a position at which a surgeon may create an incision through the soft tissue to access the exit site of the guide member from bone, to allow additional manipulations to be performed from this opposing surface region of the bone. In some examples, a distal portion 134 of the guide member, including tip 114, may be advanced out of the bone until stop structure 116 engages guide structure 118 and restricts further advancement.

A measuring device 136 may be employed to determine the length of the guide path through bone, based on the length of the guide member that is disposed outside of the bone. The guide member may have a predefined (and known) length measured from stop structure 116 to tip 114. Furthermore, guide structure 118 may have a predefined (and known) length. Accordingly, by measuring the length of distal portion 134, the length of the guide path (a length of an internal portion of the guide member disposed inside bone) may be determined (e.g., the length of the guide path equals the total length of guide member 110 minus the external (outside bone) length of the guide member (e.g., the length of guide structure 118 plus the length of external portion 134). The length of the guide path may be used, for example, to facilitate opposing hole formation and/or fastener selection, among others (see FIGS. 7 and 8).

The measuring device may have any suitable structure for measuring an axial dimension(s) of the guide member. For example, the measuring device may include a receiver structure 138 (such as a slot or bore) to receive the guide member, and a distal tip 140 to abut the bone (e.g., dorsal surface 36). The measuring device also may include indicia 142, which may be arrayed axially, such as dimension marks 144 (and/or symbols such as alphanumeric characters, among others) to indicate the measured length and/or information corresponding thereto (such as a suitable fastener/drill length, size, and/or name, among others). A measured axial dimension 146 or corresponding information may be read from the measuring device at a position aligned with distal tip 114 of the guide member. In some embodiments, the role of the measuring device may be supplemented and/or supplanted by calibration marks and other optional indicia formed on and/or added to the guide member itself.

FIG. 6 shows another exemplary approach to measuring an axial dimension of the guide path. The guide member may be inserted through bone, and its exit position from bone accessed through overlying soft tissue and identified, as described above in relation to FIG. 5. The guide member then may be retracted, shown at 148, until distal tip 114 of the guide member is substantially flush with the opposing bone surface (dorsal surface 36). An external (out of bone) proximal portion 150 of the guide member then may be measured with a measuring device 152, to allow determination of the length of the guide path, generally as described above in relation to FIG. 5. In some examples, the guide member may lack stop structure 116, so that a measuring device (such as device 148 described above) may be used to receive and measure the guide member from a proximal end of the guide member. In some examples, both distal and proximal external portions (adjacent generally opposing surface of the bone) of the guide member may be measured with a measuring device (s). In some examples, the axial dimension of the guide path may be measured directly (such as by fluoroscopy, with a measuring device (such as calipers), with a marked guide member, etc.) rather than as a difference.

FIG. 7 shows an exemplary drill 160 received over the guide member and positioned to form a hole in the bone. The drill may include a cannulated drill bit 162 that can be advanced along the guide path (over the guide wire) in an opposite direction 164 to the direction of guide path formation (see FIG. 4). In the present illustration, opposing hole formation may be performed generally in a dorsal to volar direction in the radius bone. The hole may be at least substantially concentric with the guide path and may enlarge the diameter of the guide path. The hole may extend along any suitable portion or all of the guide path through bone, for example, extending to the entry site of the guide path. In some examples, the drill bit (and/or an associated driver) may include a stop structure to define the depth to which the drill bit can be advanced into the bone, to, for example, avoid damage to the implant, particularly retention structure (such as an internal thread) of an implant opening that is aligned with the guide path. In some examples, a self-drilling fastener may form a hole as the fastener is being advanced toward the implant.

FIG. 8 shows retrograde fastener 48 after placement in a retrograde (opposing) direction 164 along the guide path such that the fastener approaches, engages, and is locked to the implant, shown at 170. A fastener that is "locked" to an implant, as used herein, is engaged with the implant (and/or another fastener engaged with the implant), such that translational motion of the fastener is restricted in both longitudinal (axial) directions of the fastener. (Rotational motion about the long axis of the locked fastener may be permitted or restricted in either rotational direction.) The fastener may lock, for example, by mating of an external thread of the fastener with a wall (an internal thread and/or lip(s)) of an implant opening. Alternatively, the fastener may lock, for example, by mating of an internal thread of the fastener with an external thread of a bridge fastener disposed in an opening of the implant and projecting into bone (see FIG. 11). (In some examples, placement of the fastener may couple the fastener to the bone plate using a locking member (such as a nut) disposed adjacent the outer surface of the bone plate.) Retrograde fastener 48 may be placed into a hole 172 that is substantially concentric with the guide path (and guide axis 102). The hole may be formed in a retrograde direction, as described in relation to FIG. 7, or may be formed in the same (forward) direction as the guide path, such as during and/or after guide path formation. In some examples, the retrograde fastener may include an axial bore (see FIG. 9) and may be placed into the bone and/or coupled with the implant over a guide member disposed in the bone, or after removal of the guide member from bone. Head 56 of the fastener may engage the bone generally opposite the implant on the bone, such as engagement with the natural bone surface and/or engagement with a recess or counterbore surface 174 formed in bone.

The retrograde fastener may be selected so that the fastener at least substantially spans the bone. The fastener also may be selected and placed so that it does not protrude excessively in regions external to the bone. The selection of the fastener may be assisted by measuring a dimension corresponding to the length of the guide path, for example, based on the length and/or position of the guide member, among others. In some examples, retrograde placement of a fastener may pull or compress one or more bone fragments toward or against the implant.

In some examples, a retrograde fastener may be placed into bone along a guide path so that the bone fastener spans a discontinuity in the bone. Accordingly, in these cases, the bone fastener may extend into bone but not completely through the bone, or may extend completely through bone. Furthermore, the retrograde fastener thus may be used for fixation without engagement with and/or coupling to another implant, such as a bone plate.

Further aspects of retrograde fastener placement, including a guide device disposed adjacent an opposing surface of bone, are described in the following patent application, which is incorporated herein by reference: Ser. No. 10/717,401, filed Nov. 19, 2003.

III. Guide Paths and Formation of Guide Paths

Guide paths may be any internal path in bone configured to guide formation of a hole/bore and/or to guide placement of a bone fastener into the bone. A guide path may be defined by structural alteration/removal of bone and/or by placement of a guide member into bone.

A guide path may have any suitable shape and size. The guide path may be linear, angular and/or arcuate, among others, but preferably is linear. The guide path may extend completely through a bone (or bones), for example, between generally opposing external surfaces of a bone or bones. Alternatively, the guide path may extend incompletely through a bone, such as from an external surface of the bone to an internal region of the bone, such as a cortex, cancellous region, or medullary canal of the bone, among others. The guide path may have a diameter (or width) that is substantially less than the diameter of a bone fastener to be placed along the guide path or may have a diameter that is about the same as or greater than the diameter of the bone fastener. In some examples, the guide path may have a diameter defined by a guide member extending along the guide path. The guide path may be hollow, that is, formed as an empty hole, or may be defined by a guide member disposed in bone, among others.

The guide path may be formed in any suitable bone(s) and between any suitable regions of the bone(s). Exemplary bones may include bones of the arms (radius, ulna, humerus), legs (femur, tibia, fibula, patella), hands/wrists (e.g., phalanges, metacarpals, and carpals), feet/ankles (e.g., phalanges, metatarsals, and tarsals), vertebrae, scapulas, pelvic bones, cranial bones, ribs, and/or clavicles, among others. In some embodiments, the guide path may be formed adjacent and/or through a proximal or distal end of a bone, i.e., in a metaphyseal and/or articular region of the bone. The guide path may start and end at any suitable surface regions of the bone, including an anterior (or volar), posterior (or dorsal), lateral, medial, proximal and/or distal region of the bone. For example, the guide path may extend from a volar to a dorsal surface region (or vice versa), from an anterior to a posterior surface region (or vice versa), from a medial to a lateral surface region (or vice versa), obliquely between adjacent surface region (e.g., volar to medial), and/or the like. In exemplary embodiments, the guide path may start in a distal portion of a radius bone, at a volar position on the radius bone, and may end at a dorsal position on the radius bone. In other exemplary embodiments, the guide path may start in a distal portion of a tibia bone, at an anterior position on the tibia bone, and may end at a posterior position on the tibia bone. Accordingly, a fastener may be directed along any of these guide paths in a forward or retrograde direction, for coupling to an implant, such as a bone plate disposed on the bone.

Guide members may have any suitable structure. Exemplary guide members may be elongate and rigid enough to be pushed and/or driven into bone. The guide members may be formed of any suitable material, including metal, plastic, ceramic, carbon fiber, etc. In exemplary embodiments, the guide members may be wires formed of metal, such as K-wires, among others. The guide members may have a tip configured to be advanced into bone, for example, a tip having a cutting edge(s) configured to cut/drill into bone. The guide members may have a predefined length. In some examples, the guide members may include reference marks and/or other indicia (such as letters and/or numbers, among others). The reference marks and/or other indicia may be configured to define axial positions along the guide members, such as to indicate lengths along each guide member. In some examples, the guide members may include an end region having a stop structure, to restrict advancement of the guide members. The stop structure may be configured to restrict advancement by contact with bone and/or by contact with a guide device for placement of the guide member, such as a channel member (for example, a cannula or drill guide, among others).

After formation of the guide path, portions of the guide path may be external to bone on one or opposing sides of the bone. In some examples, a predefined first portion and thus first length of the guide member may be external to bone on one side of the bone, and a variable, second portion and thus second length of the guide member may be external to the bone on a generally opposing side of the bone. Measurement of this second length thus may permit a determination of a third length defined by a third portion of the guide member disposed in the bone, thereby measuring the length of the guide path through the bone. A determination of the length of the guide path may permit selection of a suitable length of bone fastener.

Guide members may be placed in bone by any suitable operation. The guide members may be urged into bone translationally (e.g., pounded into bone), rotationally advanced into bone, and/or placed in a pre-formed hole in the bone, among others. In some examples, a guide member (and/or a hole-forming tool) may be placed in the bone to form a guide path, and then removed to leave a channel corresponding to the guide path.

IV. Fasteners and Fastener Placement

The fasteners generally comprise any mechanism for coupling bone fragments (and/or a bone(s)) to each other and/or to an implant, including screws, pins, and/or wires, among others.

The size and/or structure of a fastener may be selected based on any suitable parameter(s). For examples, the fastener may be selected based on the size and/or shape of a guide path; the size and/or shape of a hole formed around and/or along the guide path; the size/structure of a bone in which the fastener is to be placed; the size, shape, and/or connective structure (such as thread pitch), among others, of an opening or other connective feature of an implant that will receive the fastener; and/or the like.

The fasteners may be bone screws. Bone screws may include unicortical, bicortical, and/or cancellous bone screws, among others. Unicortical and bicortical bone screws commonly have relatively small threads for use in hard bone, such as typically found in the shaft portion of a bone, whereas cancellous bone screws commonly have relatively larger threads for use in soft bone, such as typically found near the ends (metaphyseal regions) of a long bone. Unicortical bone screws penetrate the bone cortex once, for example, adjacent a bone plate. Bicortical bone screws penetrate the bone cortex twice, for example, adjacent a bone plate and opposite the bone plate. Generally, unicortical screws provide less support than bicortical screws, because they penetrate less cortex.

In some embodiments, such as when the fasteners are configured generally as bone screws, the fasteners may include a head and an elongate shank joined to the head and extending distally from the head to a distal tip of the fastener.

The head of a fastener may have any suitable structure. The head may comprise any proximal enlargement or proximal extension of the fastener that imparts an axial asymmetry to the fastener. The head may have any suitable driver-engagement structure, such as a hexagonal socket, a single slot, a pair of slots in a cruciform arrangement, external facets, etc. In some examples, as with fasteners configured to be disposed in a forward orientation, the head may be configured to engage the implant, such as to stop advancement of the fastener, to seat the fastener against the implant, and/or to dispose the fastener in threaded engagement with the implant. In some examples, as with fasteners disposed in a retrograde orientation, the head may be configured to engage bone, spaced from the implant. In some examples, a fastener may be configured to be placed alternatively in forward and retrograde orientations.

The shank of a fastener may have any suitable structure. The shank may include an external and/or internal thread(s) and/or may include an externally nonthreaded region.

The shank may have one thread (single-threaded) or a plurality of threads (e.g., double-threaded, triple-threaded, etc.). The threads may be interspersed, so that the shank is multi-threaded, for example, to accommodate a greater pitch (a steeper thread angle). Alternatively, or in addition, the threads may be disposed on adjacent and/or nonoverlapping regions of the shank. The pitch of a thread may be constant along the shank or may change according to position, for example, decreasing closer to a head of the fastener, to provide compression of the bone as the fastener is advanced into the bone. In some examples, the threaded shank may have two or more distinct threads, with different pitches and/or diameters, such as a distal thread with a smaller (or larger) diameter and/or pitch, and a proximal thread with a larger (or smaller) diameter and/or pitch.

In some examples, the shank may have a distal external (or internal) thread configured to engage an implant. A proximal region of the shank adjacent the distal thread may be nonthreaded and/or may have a distinct thread for engagement with bone. The nonthreaded region may extend over any suitable portion of the shank, such as at least about one-half or at least about three-fourths of the distance from the head to the tip. In some examples, a region of the shank proximal to the distal thread may include a stop structure, such as a shoulder, configured to restrict advancement of the fastener, such as by contact with the implant. In some examples, the threaded shank may have an at least substantially constant pitch along the shank. In these examples, the rate of advancement of the threaded shank into bone may be at least substantially equal to the rate of advancement of the threaded shank through the implant, to restrict compression of the bone plate against the bone as the fastener is fully advanced into the implant. The pitch of a thread on a threaded shank may be selected according the structure of an aperture (of an implant) in which the threaded shank will be received, for example, based on the pitch of a thread on a wall of the aperture and/or based on vertically offset retention structures on the wall, among others. Further aspects of offset retention structures that may be suitable are described in the follow patent application, which is incorporated herein by reference: U.S. patent application Ser. No. 11/071,050, filed Feb. 28, 2005.

The threaded fasteners may have any suitable linear density of thread segments (or linear densities, if multithreaded). These densities may be measured using any suitable units, including number of thread segments per inch and/or meter, among others. For example, the fastener may have 16, 20, 24, 28, 32, 36, 40, and/or other numbers of thread segments per inch; these linear densities correspond to segment-to-segment spacings (or pitches) of 0.0625 inches, 0.0500 inches, 0.0417 inches, 0.0357 inches, 0.03125 inches, 0.0278 inches, 0.0200 inches, and/or other fractions of an inch. In some embodiments, the thread on the fastener may have a continuously and/or discontinuously varying pitch at different positions along the fastener axis. Typically, in apertures having retention structures as described above, the retention structures may be offset from one another by less than (often one half of) the segment-to-segment spacing. Thus, typical offsets may include 0.03125 inches, 0.02500 inches, 0.02083 inches, 0.01786 inches, 0.01562 inches, 0.01389 inches, 0.01250 inches, and/or other numbers of inches.

The threaded fasteners may have any suitable diameters, including major (crest-to-crest) and minor (root-to-root) diameters. In some embodiments, the major diameters may be between about 1 to 10 mm. Exemplary major diameters include 1 mm, 1.5 mm, 2.0 mm, 2.7 mm, 3.5 mm, 4.0 mm, 4.5 mm, 5.3 mm, and 6.5 mm. In some examples, the difference between the major and minor diameters (generally, twice the thread height/depth) may be between about 0.1 to 5 mm, or about 0.2 mm to 2 mm. In some examples, the major diameter and minor diameter of the threaded shank may be generally constant along the length of the shank. In some examples, these diameters may be different in proximal and distal positions of the shank.

V. Orthopedic Implants

Orthopedic implants (also termed bone-repair devices) may include, among others, any implant configured to be attached to one or more bones for repair or support of the bone(s). An implant may be an addition to the bone(s) externally (such as a bone plate) and/or internally (such as an intramedullary rod), and/or it may be a replacement for a portion or all of the bone(s) (such as a prosthesis), among others. The implant may be placed in apposition to a natural, injured, and/or engineered surface of the bone(s), such as a cut surface, among others.

Bone plates as described herein generally comprise any relatively low-profile (or plate-like) fixation device configured to stabilize at least one bone by attachment to the bone. The fixation device may be configured to span any suitable bone discontinuity so that the fixation device fixes the relative positions of bone fragments (and/or bones) disposed on opposing sides of the bone discontinuity. Alternatively, or in addition, the fixation device may provide structural support to a bone lacking a discontinuity.

Suitable discontinuities may occur naturally and/or may result from injury, disease, and/or surgical intervention, among others. Accordingly, exemplary discontinuities for use with the bone plates or other bone-repair devices described herein may include joints, fractures (breaks in bones), osteotomies (cuts in bones), and/or nonunions (for example, produced by injury, disease, or a birth defect), among others.

The implants described herein may be configured for use on any suitable bone of the human skeleton and/or of another vertebrate species. Exemplary bones may include bones of the arms (radius, ulna, humerus), legs (femur, tibia, fibula, patella), hands/wrists (e.g., phalanges, metacarpals, and carpals), feet/ankles (e.g., phalanges, metatarsals, and tarsals), vertebrae, scapulas, pelvic bones, cranial bones, ribs, and/or clavicles, among others.

The implant may be at least substantially formed of, or may include, any suitable biocompatible material(s) and/or bioresorbable material(s). Exemplary biocompatible materials that may be suitable for the implant include (1) metals/metal alloys (for example, titanium or titanium alloys, alloys with cobalt and chromium (such as cobalt-chrome), stainless steel, etc.); (2) plastics (for example, ultra-high molecular weight polyethylene (UHMWPE), polymethylmethacrylate (PMMA), polytetrafluoroethylene (PTFE), polyetheretherketone (PEEK), and/or PMMA/polyhydroxyethylmethacrylate (PHEMA)); (3) ceramics (for example, alumina, beryllia, calcium phosphate, and/or zirconia, among others); (4) composites (for example, carbon-fiber composites); (5) bioresorbable (bioabsorbable) materials or polymers (for example, polymers of α-hydroxy carboxylic acids (e.g., polylactic acid (such as PLLA, PDLLA, and/or PDLA), polyglycolic acid, lactide/glycolide copolymers, etc.), polydioxanones, polycaprolactones, polytrimethylene carbonate, polyethylene oxide, poly-β-hydroxybutyrate, poly-β-hydroxypropionate, poly-δ-valerolactone, poly(hydroxyalkanoate)s of the PHB-PHV class, other bioresorbable polyesters, and/or natural polymers (such as collagen or other polypeptides, polysaccharides (e.g., starch, cellulose, and/or chitosan), any copolymers thereof, etc.); and/or the like. In some examples, one or more of these materials may form the body of an implant and/or a coating thereon.

Each implant may include one or more openings (such as through-holes, recesses, slots, and/or concavities, among others). In some embodiments, the implant may include different openings configured to receive fasteners from opposing directions. The opposing directions may direct fasteners (1) through a bone and then to the implant, and (2) through the implant and then into the bone. Each opening may be locking or nonlocking. Locking openings may include threads or retention structures, such as offset ridges. In some embodiments, threaded openings, nuts, ridges, offset retention structures, and/or the equivalent may be used for connection of the implant to a fastener(s) directed from a generally opposing surface of a bone. In some examples, locking and/or nonlocking openings may be used for directing fasteners through the implant and then into bone. The threaded or nonthreaded openings may include or lack counterbores. Further aspects of retention structures that may be suitable are included in the following U.S. patent application, which is incorporated herein by reference: Ser. No. 11/071,050, filed Feb. 28, 2005.

The implant may have any suitable configuration for repairing a bone. The implant may be configured to be attached temporarily to a bone, for any suitable period of time, or attached permanently. In some embodiments, the implant may be configured for use on both sides of the body or on only the left or right side of the body/skeleton. When configured as a bone plate, the implant may be any plate configured to span a bone discontinuity, such as a fracture, an excision, and/or a joint, among others, to fix the relative positions of bone portions or bones on opposing sides of the discontinuity. When configured as a prosthesis, the implant may be configured to replace an articulating surface or a portion of the articulating surface.

Further aspects of bone plates that may be suitable for the system of the present teachings are included in the following U.S. patent applications, which are incorporated herein by reference: Ser. No. 10/716,719, filed Nov. 19, 2003; Ser. No. 10/717,015, filed Nov. 19, 2003; Ser. No. 10/717,399, filed Nov. 19, 2003; Ser. No. 10/717,402, filed Nov. 19, 2003; Ser. No. 10/731,173, filed Dec. 8, 2003; and Ser. No. 10/968,850, filed Oct. 18, 2004.

VI. Kits

The system of the present teachings may provide kits for bone fixation. The kits may include one or more bone plates, one or more forward fasteners, one or more retrograde fasteners, a guide member(s) (such as a wire), a guide structure or device that couples to the bone plate, a drill(s), a driver(s), a measuring device(s), one or more clamps, instructions for use, and/or the like. Some or all of the components of each kit may be provided in a sterile condition, such as packaged in a sterile container.

The kits may include a bone plate and a retrograde fastener for use with the bone plate. The retrograde fastener may have a head and a shank joined to the head and extending distally therefrom. The shank may include an external thread disposed adjacent a distal end of the shank and spaced from the head. The external thread may be figured to be received in and lock to the bone plate, through engagement with an aperture wall of the bone plate. In some examples, the kits also may include one or more forward fasteners configured to lock to the same aperture wall in a forward orientation. Further aspects of fasteners that may be suitable are described elsewhere in the present teachings, such as in Example 1, among others.

VII. EXAMPLES

The following examples describe selected aspects and embodiments of the present teachings, including methods, apparatus, and kits for retrograde placement of bone fasteners into bone. These examples and the various features and aspects thereof are included for illustration and are not intended to define or limit the entire scope of the present teachings.

Example 1

Exemplary Fasteners for Retrograde Placement

This example describes exemplary fasteners for retrograde placement into bone and for coupling to a bone plate through a leading (distal) region of the fastener; see FIGS. 9-11.

FIG. 9 shows a bone screw 180 for retrograde placement into bone. The bone screw may include a head 182 joined to a shank 184. The head may have a larger cross-sectional dimension (such as diameter) than the shank and/or may include external or internal tool-engagement structure (e.g., a hexagonal recess 186) formed axially in and/or on the head for manipulation of the bone screw with a suitable driver. Shank 184 may include a nonthreaded region 186 proximally, adjacent the head, and a threaded region 188 (with an external thread 190) distally, spaced from the head. The nonthreaded region may include a stop structure, such as a shoulder 192 or an end to the external thread, that restricts advancement of the bone screw, particularly threaded advancement. For example, the shoulder may engage the inner surface of a bone plate to stop screw advancement into/through an opening of the bone plate. The bone screw also may include an axial bore 194 for receiving a wire or other guide member.

The nonthreaded and threaded regions may have any suitable structure. The nonthreaded region may have a greater diameter, about the same diameter, or a lesser diameter than the major diameter 196 of the threaded region. Furthermore, the nonthreaded region may be shorter than, about the same length as, or longer than the length of the threaded region. In some examples, the nonthreaded region may be at least about two, five, or ten times as long as the threaded region, as measured along the long axis of the bone screw, or the nonthreaded region may be absent. Furthermore, the threaded region may have a length 198, measured axially, that is about the same as, greater than, or less than, the thickness of the implant. The threaded region may include a single external thread or a plurality of interspersed threads (a multi-threaded configuration).

FIG. 10 shows another exemplary retrograde bone screw 210. The bone screw may have include a head 212 joined distally to a shank 214. The shank may include one or more external threads extending over a substantial portion or the entire length of the shank. In some examples, the shank may include a proximal thread (or threaded region) 216 and a distal thread (or threaded region) 218. The proximal thread and the distal thread may have the same pitch (or different pitches) and may have the same or different major diameters. For example, the proximal thread may have a greater major diameter than the distal thread. Furthermore, the thread depth of the threads may be the same or different, for example, the proximal thread may have a substantially greater thread depth than the distal thread (such as to engage bone more effectively). In particular, the proximal thread may be a cancellous thread with a major diameter that is at least about 25% or about 50% greater than a minor diameter of the thread.

FIG. 11 shows yet another exemplary retrograde bone screw 230. The bone screw may include a head 232 joined distally to a shank 234. The shank may include an internal thread(s) 236 formed in a distal region 238 of the shank. The internal thread of the shank may mate with an external thread 240 provided by an implant 242 (such as a bone plate) or by a bridge fastener 244 disposed in an opening 246 of the implant. The bridge fastener may or may not be disposed in threaded engagement with the implant.

Example 2

Guide Device to Assist Fastener Placement

This example describes an exemplary guide device 260 to assist forward and/or retrograde placement of fasteners into openings of a bone plate; see FIG. 12.

Guide device 260 may mount to an implant, such as bone plate 44, using one or more apertures, such as apertures 262, 264 (see FIG. 3), and a threaded coupling member 266. Apertures 262, 264 may be spaced from other openings, particularly (distal) locking openings of the bone plate. Accordingly, each distal opening and the internal thread therein may be accessible with the guide device mounted on the bone plate.

The mounted guide device may define a plurality of guide channels 268 aligned with each of the distal openings in the head portion of bone plate 44 (see FIG. 3). Each guide channel may define a guide path that is substantially aligned with the screw (helical) axis of a distal opening. The guide channel, with or without a suitable guide insert 270 (for example, to narrow the guide channel), thus may guide forward advancement of a guide member, drill bit, and/or fastener along the guide path, to facilitate forward or retrograde fastener placement with each guide channel. The guide device, with distinct channels of the device, thus may facilitate opposing placement of fasteners that couple to the same bone plate. Further aspects of the guide device that may be suitable are described in the following patent application, which is incorporated herein by reference: U.S. patent application Ser. No. 10/968,850, filed Oct. 18, 2004.

Example 3

Retrograde Fixation of a Radial Styloid Fragment

Figure 13:
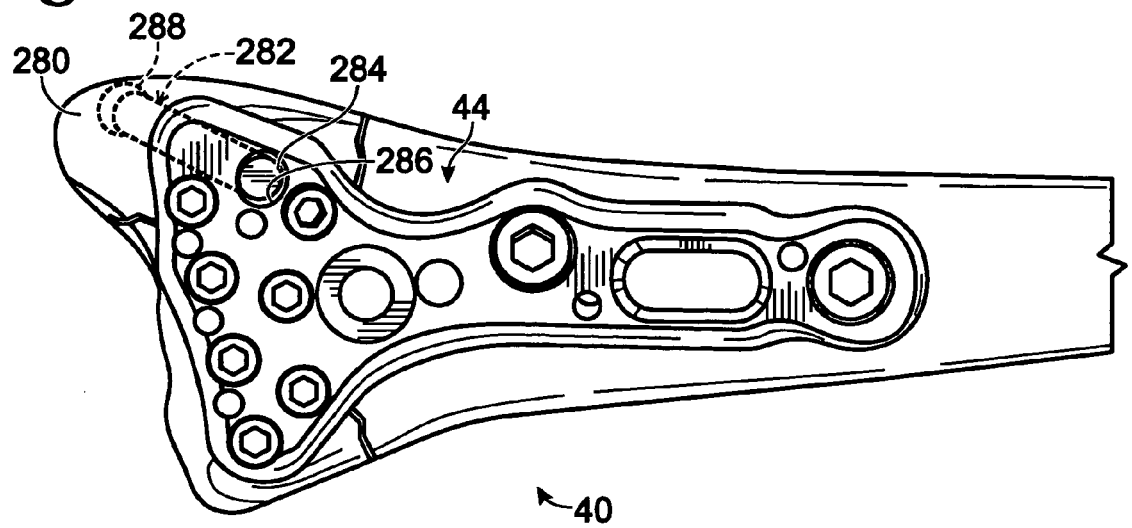
FIG. 13 is a volar view of another exemplary configuration of the system of FIG. 2, with a retrograde fastener extending to the bone plate from a styloid fragment of the radius bone, in accordance with aspects of the present teachings.
Figure 14:
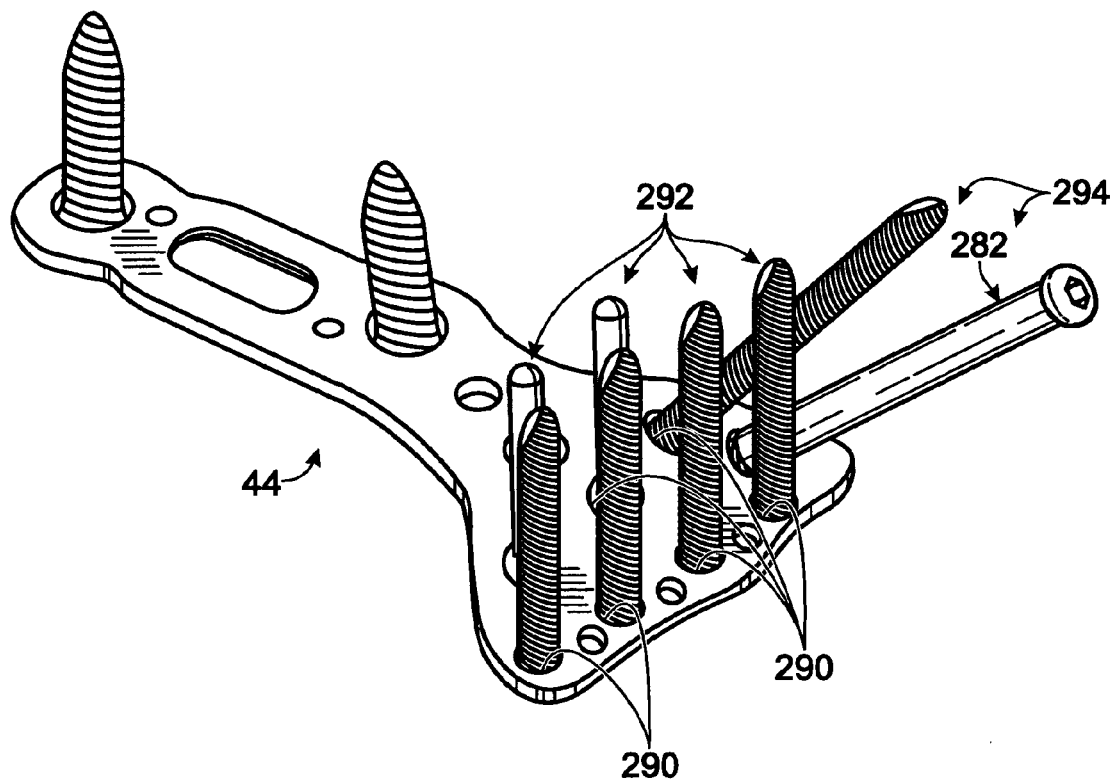
FIG. 14 is a view of the bone plate and fasteners of FIG. 13, in the absence of the radius bone, taken generally from the inner surface of the bone plate, in accordance with aspects of the present teachings.

This example describes exemplary fixation of a radial styloid fragment by retrograde placement of a fastener through the fragment and into engagement with a bone plate; see FIGS. 13 and 14.

FIG. 13 shows another exemplary configuration of system 40 (see FIGS. 2 and 3). In the present configuration, a styloid fragment 280 of the radius bone is fixed with a retrograde fastener 282, with a leading region 284 of the fastener disposed in threaded engagement with a distal opening 286 of bone plate 44. The fastener may have an oblique orientation relative to the long axis of the radius. A head 288 of the fastener thus may be disposed adjacent a distal end surface, a dorsal surface, and/or a lateral surface of the radius bone, among others.

FIG. 14 shows bone plate 44 and its coupled fasteners, including retrograde fastener 282, from the inner surface of the bone plate and without the radius bone. Any suitable combination of one or more (or all) of the openings of a bone plate, particularly distal openings 290 in a head portion of the bone plate, may be selected for forward fastener placement and/or retrograde fastener placement. Each opening selected for retrograde fastener placement may receive a fastener from a generally normal direction, shown at 292, or from an oblique direction, shown at 294.

Example 4

Selected Embodiments

This example describes selected embodiments of the present teachings, presented as a series of indexed paragraphs.

1. A kit for bone fixation, comprising: (A) a bone plate having an opening with an internal thread; and (B) first and second fasteners each having a head and a shank, the shank extending from the head and including a distal region spaced from the head, the fasteners each having an external thread configured to mate with the internal thread of the opening, the external thread being disposed on or adjacent the head of the first fastener and on the distal region of the second fastener spaced from the head, such that the first and second fasteners can be advanced into threaded engagement with the bone plate from opposing directions.

2. A kit for bone fixation, comprising: (A) a bone plate having an inner surface and an opening with a retention structure; and (B) a fastener including a head and an opposing end region having a external thread structured to engage the retention structure so that the fastener can advance into the opening and lock to the bone plate from adjacent the inner surface.

3. The kit of paragraph 2, wherein the retention structure is an internal thread.

4. The kit of paragraph 2 or 3, wherein the fastener includes a shank joined to the head and including the external thread, wherein the shank further includes a stop structure disposed proximal to the external thread and spaced from the head, and wherein the stop structure is configured to restrict advancement of the fastener into the opening from adjacent the inner surface.

5. The kit of paragraph 4, wherein the external thread is restricted to a minor portion of the shank.

6. The kit of any preceding paragraph, further comprising a guide member for forming a guide path through the bone to facilitate placement of a fastener that passes first through bone and then into contact with the bone plate.

7. The kit of paragraph 6, further comprising a measuring device for measuring the length of the guide path to facilitate selection of the fastener that passes first through bone and then into contact with the bone plate.

8. A system for bone fixation, comprising: (A) a bone plate disposed on a bone and having a plurality of openings with an internal thread; and (B) fasteners disposed in threaded engagement with the internal threads, at least two of the fasteners having at least substantially opposite orientations in the bone.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

I claim:

1. A method of coupling a fastener to a bone plate defining a plurality of openings, comprising:
   attaching the bone plate to a bone;
   forming a guide path by placing a wire through the bone from an opening of the attached bone plate;
   placing the fastener along the guide path in an opposing direction relative to the step of forming a guide path; and
   locking a leading region of the fastener to the attached bone plate at the opening,
   wherein the fastener has a stop structure formed proximal to the leading region, and wherein the step of locking a leading region of the fastener includes a step of advancing the leading region into the opening of the bone plate until the stop structure engages the bone plate and restricts further advancement of the fastener.

2. The method of claim 1, wherein the step of attaching the bone plate includes a step of attaching the bone plate to the bone with one or more threaded fasteners.

3. The method of claim 1, wherein the step of attaching the bone plate includes a step of attaching the bone plate to a radius bone.

4. The method of claim 3, wherein the step of placing the fastener includes a step of placing the fastener through a styloid fragment of the radius bone.

5. The method of claim 1, wherein the opening includes an internal thread, and wherein the step of locking disposes the leading region of the fastener in threaded engagement with the internal thread.

6. The method of claim 1, the guide path having a length through the bone, the method further comprising:
   determining the length of the guide path; and
   selecting the fastener based on the length for use in the step of placing the fastener.

7. The method of claim 1, wherein the step of attaching the bone plate includes a step of placing one or more bone screws into the bone from one or more of the openings.

8. The method of claim 1, further comprising a step of forming a hole in the bone in the opposing direction using the wire as a guide, wherein the step of placing the fastener along the guide path includes a step of placing the fastener into the hole.

9. A method of directing a fastener to a bone plate defining a plurality of openings, comprising:

attaching the bone plate to a bone;
forming a guide path by placing a wire through the bone from an opening of the attached bone plate;
forming a hole in the bone along the wire in an opposing direction relative to the step of forming a guide path;
placing the fastener into the hole in the opposing direction; and
coupling a leading region of the fastener to the attached bone plate by engagement of the fastener with the bone plate at the opening,
wherein the fastener has a stop structure formed proximal to the leading region, and wherein the step of coupling a leading region of the fastener includes a step of advancing the leading region into the opening of the bone plate until the stop structure engages the bone plate and restricts further advancement of the fastener.

10. The method of claim 9, wherein the stop structure is a shoulder.

11. The method of claim 9, wherein the step of attaching the bone plate includes a step of attaching the bone plate to a radius bone adjacent a distal volar surface region of the radius bone.

12. The method of claim 9, wherein the opening includes an internal thread, and wherein the step of coupling a leading region of the fastener disposes the leading region in threaded engagement with the internal thread.

13. The method of claim 9, wherein the guide path has a length through the bone, the method further comprising:
   determining the length of the guide path; and
   selecting the fastener based on the length.

14. The method of claim 9, wherein the step of attaching the bone plate includes a step of placing one or more bone screws into the bone from one or more of the openings.

15. A method of coupling a fastener to a bone plate defining a plurality of openings, comprising:
   attaching the bone plate to a radius bone adjacent a volar surface region of the radius bone;
   placing a wire through the radius bone from an opening of the attached bone plate, to define an axis;
   placing the fastener along the axis in an opposing direction relative to the step of placing a wire; and
   locking a leading region of the fastener to the attached bone plate at the opening,
   wherein the fastener has a stop structure formed proximal to the leading region, and wherein the step of locking a leading region of the fastener includes a step of advancing the leading region into the opening of the bone plate until the stop structure engages the bone plate and restricts further advancement of the fastener.

16. The method of claim 15, wherein the step of attaching the bone plate includes a step of attaching the bone plate to the radius bone with one or more bone screws.

17. The method of claim 15, wherein the step of placing a wire includes a step of placing the wire into the radius bone from a volar surface position of the radius bone such that the wire exits the radius bone at a dorsal surface position of the radius bone.

18. The method of claim 15, wherein the step of placing the fastener includes a step of placing the fastener through a styloid fragment of the radius bone.

19. The method of claim 15, wherein the step of placing the fastener includes a step of placing the fastener into a hole formed in the opposing direction along the wire.

20. The method of claim 15, wherein the step of attaching the bone plate includes a step of placing one or more bone screws into the radius bone from one or more of the openings.

* * * * *